(12) United States Patent
Müller et al.

(10) Patent No.: US 11,103,733 B2
(45) Date of Patent: Aug. 31, 2021

(54) WATER BASED CONCENTRATED PRODUCT FORMS OF OIL-SOLUBLE ORGANIC UV ABSORBERS

(75) Inventors: Stefan Müller, Weil am Rhein (DE); Brigitte Lindemann, Grenzach-Wyhlen (DE); Bernd Herzog, Grenzach-Wyhlen (DE)

(73) Assignee: BASF SE, Ludwigshafen (DE)

( * ) Notice: Subject to any disclaimer, the term of this patent is extended or adjusted under 35 U.S.C. 154(b) by 354 days.

(21) Appl. No.: 12/664,666

(22) PCT Filed: Jun. 30, 2008

(86) PCT No.: PCT/EP2008/058356
§ 371 (c)(1),
(2), (4) Date: Jun. 4, 2010

(87) PCT Pub. No.: WO2009/007264
PCT Pub. Date: Jan. 15, 2009

(65) Prior Publication Data
US 2010/0284950 A1 Nov. 11, 2010

(30) Foreign Application Priority Data

Jul. 9, 2007 (EP) .................................. 07112033
Oct. 19, 2007 (EP) .................................. 07118883
Mar. 6, 2008 (EP) .................................. 08152378

(51) Int. Cl.
| | | |
|---|---|---|
| *A61Q 17/04* | (2006.01) | |
| *A61K 8/11* | (2006.01) | |
| *A61K 8/58* | (2006.01) | |
| *A61K 8/37* | (2006.01) | |
| *A61K 8/35* | (2006.01) | |
| *A61K 8/44* | (2006.01) | |
| *A61K 8/81* | (2006.01) | |
| *A61K 8/893* | (2006.01) | |
| *A61K 8/49* | (2006.01) | |

(52) U.S. Cl.
CPC ............... *A61Q 17/04* (2013.01); *A61K 8/11* (2013.01); *A61K 8/35* (2013.01); *A61K 8/37* (2013.01); *A61K 8/44* (2013.01); *A61K 8/445* (2013.01); *A61K 8/496* (2013.01); *A61K 8/4966* (2013.01); *A61K 8/585* (2013.01); *A61K 8/8152* (2013.01); *A61K 8/893* (2013.01); *A61K 2800/413* (2013.01)

(58) Field of Classification Search
None
See application file for complete search history.

(56) References Cited

U.S. PATENT DOCUMENTS

| | | | |
|---|---|---|---|
| 4,724,240 A | 2/1988 | Abrutyn | |
| 6,214,929 B1 | 4/2001 | Haremza et al. | |
| 6,338,838 B1 | 1/2002 | Berset et al. | |
| 2001/0022965 A1* | 9/2001 | Heger | A61K 8/042 424/59 |
| 2002/0131941 A1 | 9/2002 | Habeck et al. | |
| 2003/0235539 A1* | 12/2003 | Mongiat et al. | 424/59 |
| 2004/0057912 A1* | 3/2004 | Bonda et al. | 424/59 |
| 2006/0002964 A9* | 1/2006 | Schreiber | A61K 8/042 424/401 |
| 2006/0287416 A1* | 12/2006 | Schellenberg et al. | 524/100 |
| 2007/0218089 A1* | 9/2007 | Dyllick-Brenzinger | C08F 2/22 424/401 |
| 2008/0167189 A1* | 7/2008 | Oetter | C08G 18/283 504/360 |

(Continued)

FOREIGN PATENT DOCUMENTS

| | | |
|---|---|---|
| DE | 19810268 A1 | 9/1999 |
| DE | 10046927 A1 | 4/2002 |

(Continued)

OTHER PUBLICATIONS

Sigma-Aldrich, a product comparison guide at www.sigmaaldrich.com [retrieved on Dec. 31, 2015]. Retrieved from the Internet: <URL: http://www.sigmaaldrich.com/catalog/substance/bemotrizinol6278118739300611 ?lang=en&region=US>.*

Pubchem, a compound database at pubchem.ncbi.nlm.nih.gov [retrieved on Dec. 31, 2015]. Retrieved from the Internet: <URL: http://pubchem.ncbi.nlm.nih.gov/compound/11954320#section=Top>.*

(Continued)

*Primary Examiner* — David J Blanchard
*Assistant Examiner* — John P Nguyen
(74) *Attorney, Agent, or Firm* — Marshall, Gerstein & Borun LLP

(57) ABSTRACT

The instant invention refers to the use of a concentrated aqueous polymer dispersion with an average particle size of less than 1000 nm comprising (a) a polymer carrier prepared by heterophase radical polymerization of at least one ethylenically unsaturated monomer in the presence of (b) an oil-soluble organic UV absorber selected from the class of p-aminobenzoic acid derivatives; salicylic acid derivatives; benzophenone derivatives; diphenyl acrylate derivatives; benzofuran derivatives; polymeric UV absorbers, comprising one or more organosilicon radicals; cinnamic acid derivatives; camphor derivatives; s-triazine derivatives; tri-anilino-s-triazine derivatives; menthyl anthranilates; and benzotriazole derivatives; wherein the weight ratio of the oil-soluble organic UV absorber (b) to polymer carrier (a) is greater than 50 parts UV absorber per 100 parts of carrier; for the protection of human and animal hair and skin against the damaging effect of UV radiation. The concentrated aqueous polymer dispersions show unexpectedly high sunscreen effects and a positive skin feeling.

8 Claims, No Drawings

(56) References Cited

U.S. PATENT DOCUMENTS

2008/0247975 A1* 10/2008 Dueva-Koganov ......................... A61K 8/8152
424/59
2010/0266517 A1* 10/2010 Dingley et al. ................ 424/59

FOREIGN PATENT DOCUMENTS

| EP | 1051963 A | 11/2000 |
|----|-----------|---------|
| JP | 5238924 A | 9/1993 |
| JP | 9118726 A | 5/1997 |
| WO | 2005/023878 A | 3/2005 |
| WO | WO 2005023878 A1 * | 3/2005 |

OTHER PUBLICATIONS

D'Ruiz, "TINSORB® S", Ciba Specialty Chemicals Corporation, pp. 1-22, 2000.*
English language abstract of JP 9118726 printed on Mar. 3, 2010.
English language abstract of JP 5238924 printed on Mar. 3, 2010.

* cited by examiner

WATER BASED CONCENTRATED PRODUCT FORMS OF OIL-SOLUBLE ORGANIC UV ABSORBERS

The instant invention pertains to a concentrated aqueous polymer dispersion with a particle size of less than 1000 nm containing oil-soluble organic UV absorbers, prepared by heterophase radical polymerization of ethylenically unsaturated monomers in the presence of the UV absorbers, wherein the weight ratio of UV absorbers to polymeric carrier is greater than 50 parts UV absorbers per 100 parts polymer carrier.

Another aspect of the invention is a process for the preparation of such aqueous dispersions with UV absorber content. Aqueous dispersions prepared according to this process are useful ingredients for cosmetic applications, preferably sunscreens.

Only a small number of registered UV filters exist for cosmetic UV protection in the aqueous phase. Unfortunately the use of these UV absorbers is highly limited. For example the well known UV absorber Phenylbenzimidazole Sulfonic Acid (PBSA) can only be used in a very small pH range >7.2. Formulations featuring a skin neutral pH are therefore not accessible with these UV filters.

Simultaneously it is well known that the balanced combination of UV filters in the oil- and water phase shows a particular high protection effect compared to formulations which comprise only UV filters in the oil- or water phase. Such formulations, however, show only little water resistance.

It has now been found that concentrated aqueous polymer dispersions with a particle size of less than 1000 nm, which are prepared by heterophase radical polymerization of ethylenecally unsaturated monomers in the presence of UV absorbers, wherein the weight ratio between UV absorber and polymer carrier is greater than 50 parts of UV absorber to 100 parts of the polymer carrier, show unexpectedly high sunscreen effects and a positive skin feeling.

One aspect of the invention is the use of a concentrated aqueous polymer dispersion with an average particle size of less than 1000 nm comprising
  (a) a polymer carrier prepared by heterophase radical polymerization of at least one ethylenically unsaturated monomer in the presence of
  (b) an oil-soluble organic UV absorber selected from the class of p-aminobenzoic acid derivatives; salicylic acid derivatives; benzophenone derivatives; diphenyl acrylate derivatives; benzofuran derivatives; polymeric UV absorbers, comprising one or more organosilicon radicals; cinnamic acid derivatives; camphor derivatives; s-triazine derivatives; trianilino-s-triazine derivatives; menthyl anthranilates; and benzotriazole derivatives;
wherein the weight ratio of the oil-soluble organic UV absorber (b) to polymer carrier (a) is greater than 50 parts UV absorber per 100 parts of carrier;
for the protection of human and animal hair and skin against the damaging effect of UV radiation.

Preferably the concentration of the polymer carrier with the oil-soluble organic UV absorber in the dispersion is from 20% to 60% b.w.

Optionally a non-ionic, cationic or anionic surfactant, preferably a non-ionic or cationic may be added.

Preferably more than one ethylenically unsaturated monomer is used. When the polymerization is carried out with two or more monomers, at least one monomer may carry two unsaturated functionalities in order to provide a certain degree of crosslinking. For example the amount of the difunctional monomer may vary from 0.5 to 20% by weight based on the total weight of the monomer mixture.

Preferred is the use of a concentrated aqueous polymer dispersion wherein the weight ratio of oil-soluble organic UV absorber to polymer carrier is equal or greater than 80 parts per 100 parts, more preferred greater 100 parts per 100 parts and most preferred greater 120 parts per 100 parts.

In a specific embodiment of the invention, the weight ratio of the oil-soluble UV absorber to polymer carrier is from 500 parts of the UV absorber per 100 parts of polymer carrier to 100 parts of the UV absorber to 100 parts of polymer carrier.

Preferably the average particle size is less than 500 nm, more preferably less than 250 nm.

Droplet (oil/water emulsion) as well as particle (polymer dispersion) size can be measured by using dynamic light scattering (DLS) technique (also known as photon correlation spectroscopy (PSC) or quasi-elastic light scattering (QELS)). For this kind of measurement a NICOMP particle size (NICOMP Model 380, Particle Sizing System, Santa Barbara, Calif., USA) with a fixed scattering angle of 90° can be used for example. The measurement leads to the mean diameter $D_{INT}$ (intensity weighted).

The total solids content of the concentrated aqueous polymer dispersion is for example more than 20%, for instance more than 30% and preferably more than 40% by weight based on the total weight of the aqueous dispersion. In a particularly preferred embodiment the total solids content is more than 50% by weight based on the total weight of the aqueous dispersion.

Oil-soluble UV absorbers used as component (b) in the present invention are selected from different classes of well-known organic UV filters. Such protective substances are described, for example, in GB-A-2,286,774 or alternatively are known from Cosmetics & Toiletries (107), 50 et seq. (1992).

The following compounds are examples of p-aminobenzoic acid derivatives:

4-aminobenzoic acid (PABA); ethyldihydroxypropyl-PABA of formula

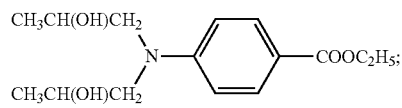

PEG-25-PABA of formula

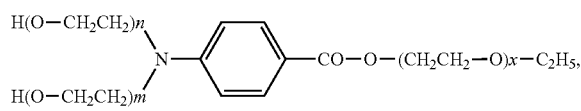

wherein m, n and x have the same meaning and are each a maximum of 25; octyldimethyl PABA of formula

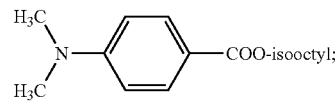

and glycyl aminobenzoate of formula

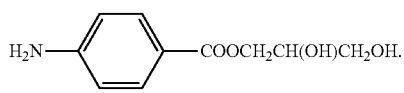

The following compounds are examples of salicylic acid derivatives:

homomenthyl salicylate of formula

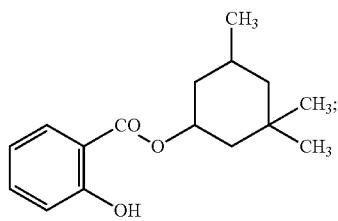 [SMILES: CC1CC(OC(=O)c2ccccc2O)CC(C)(C)C1]

triethanolamine salicylate of formula

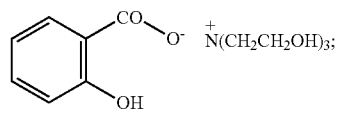

amyl p-dimethylaminobenzoate of formula

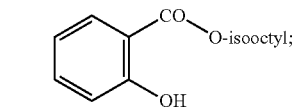

octyl salicylate of formula and 4-isopropylbenzyl salicylate of formula

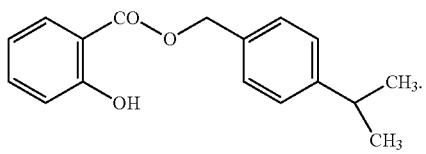 [SMILES: CC(C)c1ccc(COC(=O)c2ccccc2O)cc1]

The following compounds are examples of benzophenone derivatives:
benzophenone-3-(2-hydroxy-4-methoxybenzophenone), benzophenone-4-(2-hydroxy-4-methoxybenzophenone-5-sulfonic acid) and benzophenone-8-(2,2'-dihydroxy-4-methoxy-benzophenone).

The following compounds are examples of diphenyl acrylate derivatives:
octocrylene(2-ethylhexyl-2-cyano-3,3'-diphenyl acrylate) and octocrylene (ethyl-2-cyano-3,3'-diphenyl acrylate).

The following compounds are examples of benzofuran derivatives:
3-(benzofuranyl)-2-cyanoacrylate, 2-(2-benzofuranyl)-5-tert-butylbenzoxazole and 2-(p-aminophenyl)benzofuran and especially the compound of formula

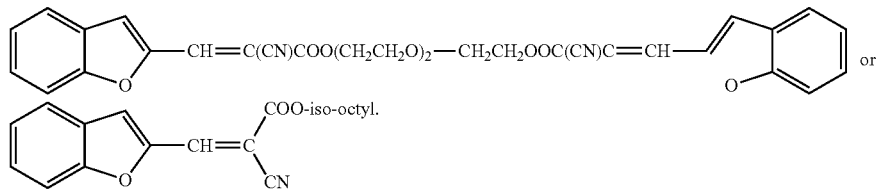

The following compounds are examples of polymeric UV absorbers that contain one or more organosilicon radicals:

a benzylidene malonate derivative, especially the compound of formula

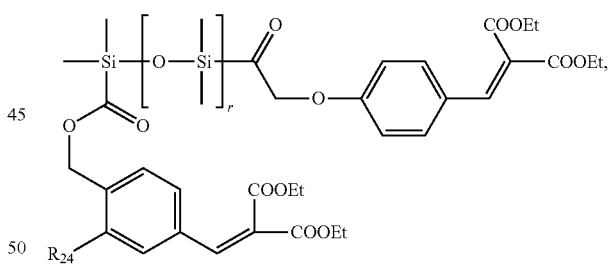

wherein $R_{24}$ is hydrogen or methoxy and r is approximately 7; the compound of formula

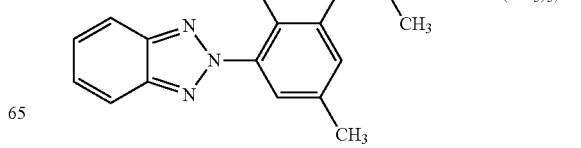

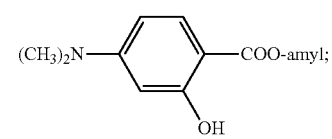

-continued

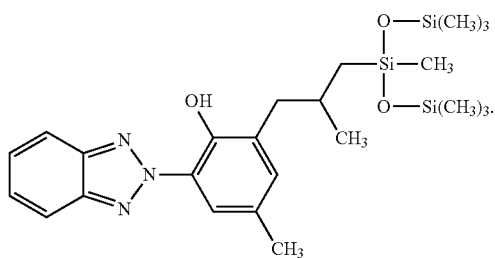

The following compounds are examples of cinnamic acid esters:

Octyl methoxycinnamate(4-methoxycinnamic acid 2-ethylhexyl ester), diethanolamine methoxycinnamate (diethanolamine salt of 4-methoxycinnamic acid), isoamyl p-methoxy-cinnamate (4-ethoxycinnamic acid 2-isoamyl ester), 2,5-diisopropylmethyl cinnamate and a cinnamic acid amido derivative.

The following compounds are examples of camphor derivatives:

4-methyl-benzylidene camphor[3-(4'-methyl)benzylidene-bornan-2-one], 3-benzylidene camphor(3-benzylidene-bornan-2-one), polyacrylamidomethylbenzylidene camphor {N-[2(and 4)-2-oxyborn-3-ylidene-methyl)benzyl] acrylamide polymer}, trimonium-benzylidene camphor sulfate[3-(4'-trimethylammonium)-benzylidene-bornan-2-one methyl sulfate], terephthalydene dicamphorsulfonic acid {3,3'-(1,4-phenylenedimethine)-bis(7,7-dimethyl-2-oxo-bicyclo[2.2.1]heptane-1-methanesulfonic acid} or salts thereof, and benzylidene camphorsulfonic acid [3-(4'-sulfo) benzylidenebornan-2-one] or salts thereof.

The following compounds are examples of trianilino-s-triazine derivatives:

octyl triazine-[2,4,6-trianilino-(p-carbo-2'-ethyl-1'-oxy)-1,3,5-triazine, and the trianilino-s-triazine derivatives described in U.S. Pat. Nos. 5,332,568, 5,252,323, WO 93/17002 and WO 97/03642 and EP-A-0 517 104.

The following compound is an example of s-triazine compounds:

2-(4'-methoxyphenyl)-4,6-bis(2'-hydroxy-4'-n-octyloxyphenyl)-1,3,5-triazine; 2,4-bis{[4-(3-(2-propyloxy)-2-hydroxypropyloxy)-2-hydroxy]phenyl}-6-(4-methoxyphenyl)-1,3,5-triazine; 2,4-bis{[4-(2-ethylhexyloxy)-2-hydroxy]phenyl}-6-[4-(2-methoxyethylcarboxyl) phenylamino]-1,3,5-triazine; 2,4-bis{[4-(tris (trimethylsiloxysilylpropyloxy)-2-hydroxy]phenyl}-6-(4-methoxyphenyl)-1,3,5-triazine; 2,4-bis{[4-(2"methylpropenyloxy)-2-hydroxy]phenyl}-6-(4-methoxyphenyl)-1,3,5-triazine; 2,4-bis{[4-(1',1',1',3',5',5', 5'-heptamethyltrisilyl-2"-methylpropyloxy)-2-hydroxy] phenyl}-6-(4-methoxyphenyl)-1,3,5-triazine; 2,4-bis{[4-(3-(2-propyloxy)-2-hydroxy-propyloxy)-2-hydroxy]phenyl}-6-[4-ethylcarboxylphenylamino]-1,3,5-triazine; or 2,4-bis{ [4-(2-ethylhexyloxy)-2-hydroxy]phenyl}-6-(1-methylpyrrol-2-yl)-1,3,5-triazine.

The following compound is an example of a benzotriazole:

2-(2-hydroxy-5-methyl-phenyl)benzotriazole and Benzotriazolyl Dodecyl p-Cresol.

In a preferred embodiment of the present invention the following UV absorbers are used:

($b_1$) Ethylhexyl Methoxycinnnamate of formula (1)

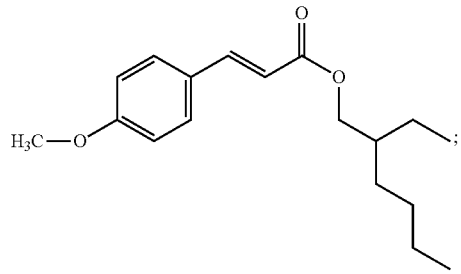 [SMILES: CCCCC(CC)COC(=O)/C=C/c1ccc(OC)cc1]

($b_2$) Bis-Ethylhexyloxyphenol Methoxyphenyl Triazine of formula (2)

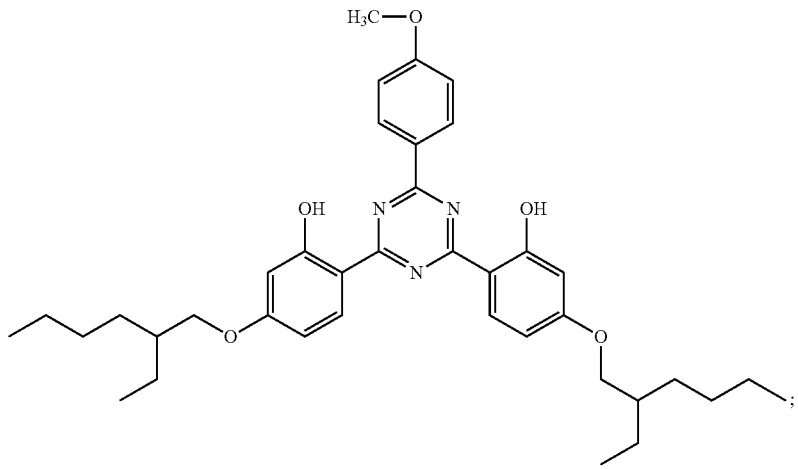 [SMILES: CCCCC(CC)COc1ccc(-c2nc(-c3ccc(OC)cc3)nc(-c3ccc(OCC(CC)CCCC)cc3O)n2)c(O)c1]

(b₃) Benzotriazolyl Dodecyl p-Cresol of formula (3)
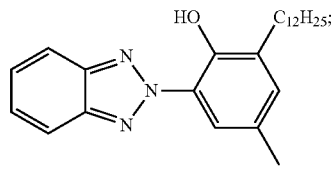
(b₄) Butyl Methoxydibenzoyl Methane of formula (4)
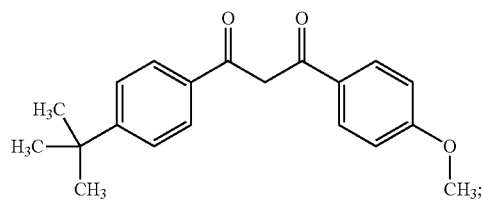 [SMILES: COc1ccc(C(=O)CC(=O)c2ccc(C(C)(C)C)cc2)cc1]
(b₅) 2-Cyan-3,3-diphenylacrylic acid (2-ehtylhexylester) of formula (5)
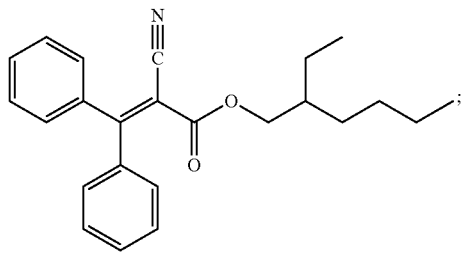 [SMILES: CCCCC(CC)COC(=O)C(C#N)=C(c1ccccc1)c1ccccc1]
(b₆) Tris-Ethylhexyloxyphenol Methoxyphenyl Triazine of formula (6)
(b₇) Benzophenone-3 of formula (7)
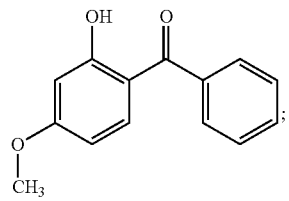
(b₈) Benzophenone-4 of formula (8)
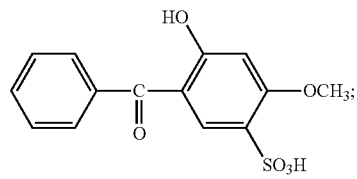
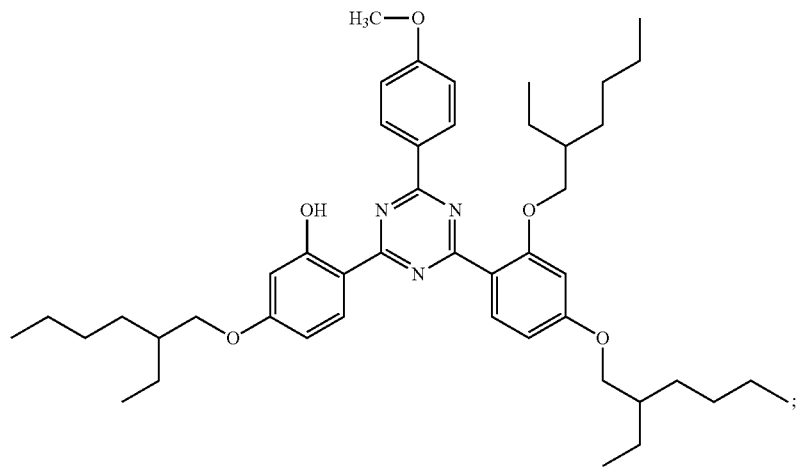 [SMILES: CCCCC(CC)COc1ccc(-c2nc(-c3ccc(OC)cc3)nc(-c3ccc(OCC(CC)CCCC)cc3OCC(CC)CCCC)n2)c(O)c1]

(b₉) polysilicone-15 of formula (9)
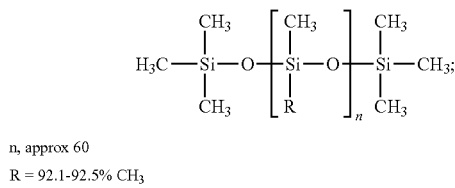
n, approx 60
R = 92.1-92.5% CH₃
(b₁₀)
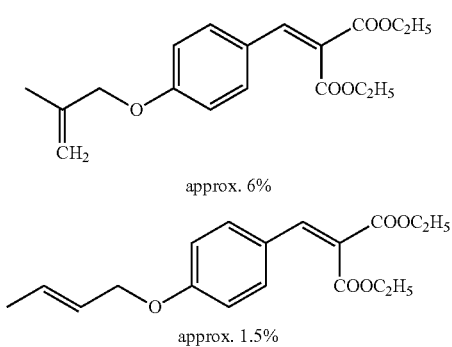
approx. 6%
approx. 1.5%
Diethylamino Hydroxy Benzoyl Hexyl Benzoate of formula (10)
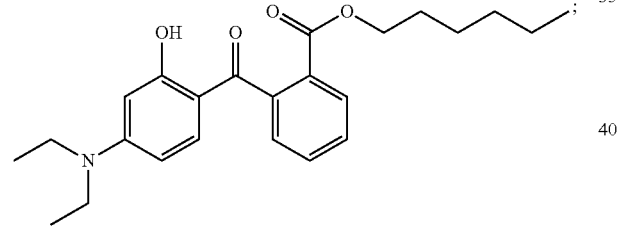
(b₁₁) Diethylhexyl Butamido Triazone of formula (11)
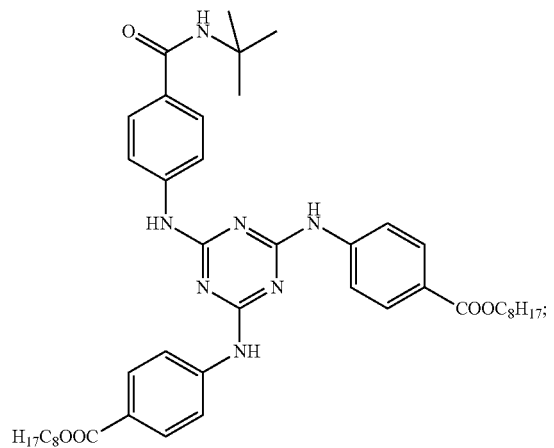
(b₁₂) Drometrizole Trisiloxane of formula (12)
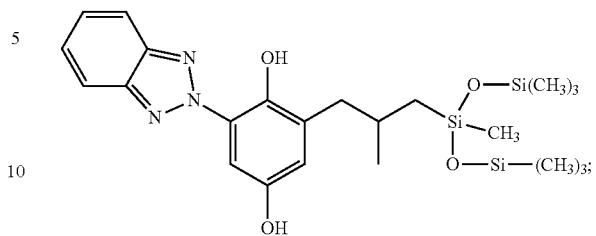
(b₁₃) Ethylhexyl Dimethyl PABA of formula (13)
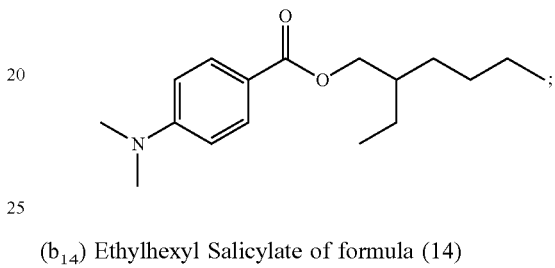
(b₁₄) Ethylhexyl Salicylate of formula (14)
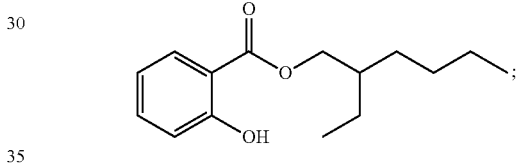
(b₁₅) Ethylhexyl Triazone of formula (15)
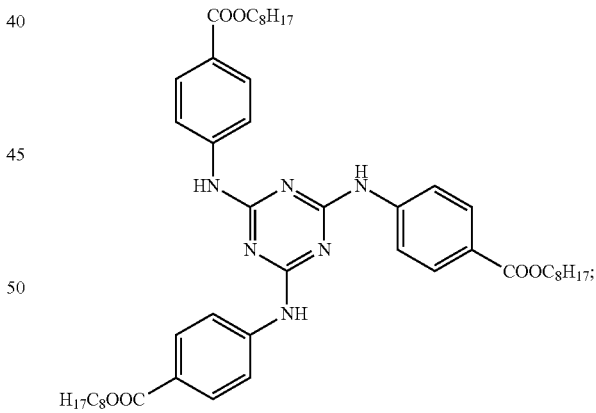
(b₁₆) Homosalate of formula (16)
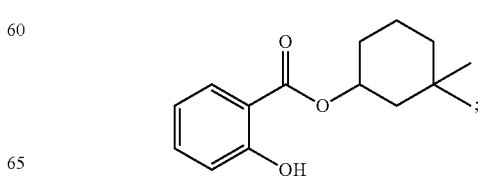

($b_{17}$) Isoamyl p-Methoxycinnamate of formula (17)

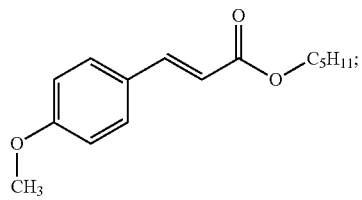

($b_{18}$) 4-Methylbenzylidene Camphor of formula (18)

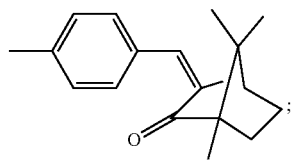 [SMILES: C/C(=C/c1ccc(C)cc1)C(=O)C1(C)CCCC1(C)C]

or mixtures of ($b_1$) to ($b_{18}$).

Preferably the UV absorber ($b_2$) of formula (2) is used.

In a preferred embodiment of the present invention mixtures of UV absorbers are used.

The following mixtures of UV absorbers are preferably used:
mixture of the UV absorbers ($b_1$), ($b_2$) and ($b_3$) of formula (1), (2) and (3)
mixture of the UV absorbers ($b_4$) and ($b_5$) of formula (4) and (5);
mixture of the UV absorbers ($b_1$) and ($b_2$) of formula (1) and (2);
mixture of the UV absorbers ($b_2$) and ($b_6$) of formula (2) and (6);
mixture of the UV absorbers of formula ($b_2$) and ($b_3$) (2) and (3);
mixture of the UV absorbers ($b_2$), ($b_3$) and ($b_6$) of formula (2), (3) and (6).

In a preferred embodiment the oil-soluble organic UV absorber (b) has water solubility of less than 1%, preferably less than 0.1% and most preferably of less than 0.01% by weight at room temperature and atmospheric pressure.

The right balance between solubility in water and solubility in the monomer droplets has a strong influence on the polymerization result. Therefore the polarity of the oil-soluble organic UV absorber can also be expressed in terms of log p.

The partition coefficient log p (octanol/water) is a widely used parameter for example in rating the environmental impact of chemical compounds. Its calculation is described by W. M. Meylan, P. H. Howard in J. Pharmaceutical Sciences 84, (1995), 83-92.

In the context of the present invention the oil-soluble organic UV absorber has preferably a log p value of more than log p=2.

For example the ethylenically unsaturated monomer is selected from the group consisting of styrene, substituted styrene, conjugated dienes, acrolein, vinyl acetate, vinylpyrrolidone, vinylimidazole, maleic anhydride, (alkyl)acrylic acid anhydrides, (alkyl)acrylic acid salts, (alkyl)acrylic esters, (alkyl)acrylonitriles, (alkyl)acrylamides, vinyl halides or vinylidene halides.

For instance the ethylenically unsaturated monomer is a compound of formula (19) $CH_2=C(R_a)-(C=Z)-R_b$, wherein Z is O or S;

$R_a$ is hydrogen; or $C_1$-$C_4$alkyl;

$R_b$ is $NH_2$; $O^-(Me^+)$; glycidyl; unsubstituted $C_1$-$C_{18}$alkoxy; $C_2$-$C_{100}$alkoxy interrupted by at least one N and/or O atom, or hydroxy-substituted $C_1$-$C_{18}$alkoxy; unsubstituted $C_1$-$C_{18}$alkylamino; di($C_1$-$C_{18}$alkyl)amino; hydroxy-substituted $C_1$-$C_{18}$alkylamino or hydroxy-substituted di($C_1$-$C_{18}$alkyl)amino; $-O-CH_2-CH_2-N(CH_3)_2$; or $-O-CH_2-CH_2-N^+H(CH_3)_2An^-$;

$An^-$ is a anion of a monovalent organic or inorganic acid; and

Me is a monovalent metal atom or the ammonium ion.

Examples for specific ethylenically unsaturated monomers are styrene, iso-butylmethacrylate, cyclohexylmethacrylate, hydroxyethylmethacrylate, methylmethacrylate, benzylmethacrylate, vinyl toluene, n-butylacrylate, tert-butylacrylate, methylacrylate, ethylacrylate, propylacrylate, hexylacrylate or hydroxyethylacrylate.

A particular suitable monomer mixture is a mixture of hydroxyethylmethacrylate, methylmethacrylate, cyclohexylmethacrylate, vinyl toluene, methylmethacrylate, iso-buylmethacrylate.

Examples of acids from which the anion $An^-$ is derived are $C_1$-$C_{12}$carboxylic acids, organic sulfonic acids such as $CF_3SO_3H$ or $CH_3SO_3H$, mineralic acids such as HCl, HBr or HI, oxo acids such as $HClO_4$ or complex acids such as $HPF_6$ or $HBF_4$.

Examples for $R_a$ as $C_2$-$C_{100}$alkoxy interrupted by at least one O atom are of formula

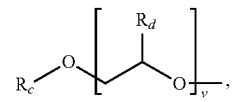

wherein $R_c$ is $C_1$-$C_{25}$alkyl, phenyl or phenyl substituted by $C_1$-$C_{18}$alkyl, and $R_d$ is hydrogen or methyl and v is a number from 1 to 50.

These monomers are for example derived from non ionic surfactants by acrylation of the corresponding alkoxylated alcohols or phenols. The repeating units may be derived from ethylene oxide, propylene oxide or mixtures of both.

Further examples of suitable acrylate or methacrylate monomers are given below.

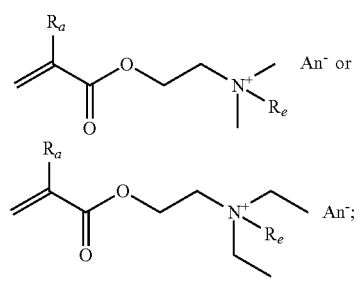

wherein $An^-$ and $R_a$ have the meaning as defined above and $R_e$ is methyl or benzyl.

$An^-$ is preferably $Cl^-$, $Br^-$ or $^-O_3S-CH_3$.

Further acrylate monomers are

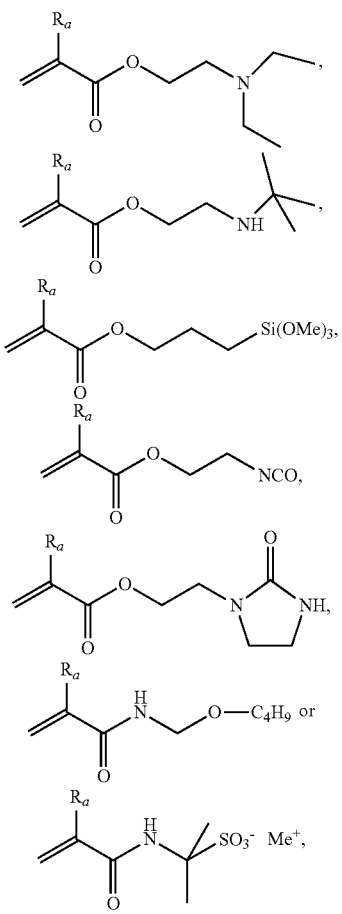

wherein
R$_a$ is defined as I formula (19).
Examples for suitable monomers other than acrylates are

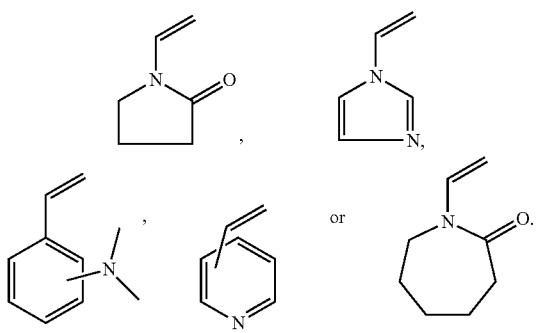

Preferably
R$_a$ is hydrogen; or methyl,
R$_b$ is NH$_2$, glycidyl; unsubstituted or hydroxy substituted C$_1$-C$_4$alkoxy; unsubstituted C$_1$-C$_4$alkylamino; di(C$_1$-C$_4$alkyl)amino; hydroxy-substituted C$_1$-C$_4$alkylamino; or hydroxy-substituted di(C$_1$-C$_4$alkyl)amino; and
Z is oxygen.
Acrylic acid esters and methacrylic acid esters are typically C$_1$-C$_{18}$alkyl esters.

Preferred is a concentrated aqueous polymer dispersion wherein the ethylenically unsaturated monomer is selected from the group consisting of C$_1$-C$_{18}$acrylates, C$_1$-C$_{18}$methacrylates, acrylic acid, (meth)acrylic acid, styrene, vinyltoluene, hydroxy-functional acrylates or (meth)acrylates, acrylates or (meth)acrylates derived from alkoxylated alcohols and multifunctional acrylates or (meth)acrylates or mixtures thereof.

Particularly useful methacrylates are iso-butylmethacrylate, cyclohexylmethacrylate.

In a specific embodiment the concentrated aqueous polymer dispersion is prepared from a mixture of at least two of the above monomers and at least one monomer which is bifunctional or multifunctional, so that a crosslinked polymer is obtained. The amount of bi- or multi-functional monomer is for example from 0.5 to 20 weight-%, based on the weight of the sum of monomers.

Typical examples for bi- or multifunctional monomers are divinyl-benzene, ethylenglycol diacrylate, butylenglycol diacrylate, diethyleneglycol diacrylate, Trimethylolpropan triacrylate, Trimethylolpropan-ethoxylate (1EO/OH)-triacrylate, Glycerin-propoxylate (1PO/OH) triacrylate, Pentaerythritol-propoxylat-triacrylate, Pentaerythritol-triacrylate (PETIA), Trimethylolpropantriacrylate (TMPTA), or Pentaerythritoltetraacrylate (PETA).

The monomers or monomer mixtures have preferably a low water solubility, which is below 5%, more preferred below 0.5% and most preferred below 0.1% by weight.

The preparation of a concentrated aqueous polymer dispersion with an average particle size of less than 1000 nm is prepared in a manner known per se as disclosed for example in WO 2005/23878, comprising the step of polymerizing at least one ethylenically unsaturated monomer in the presence of an oil-soluble organic UV absorber by heterophase radical polymerization; wherein the weight ratio of organic oil-soluble organic UV absorber to polymer carrier formed from the ethylenically unsaturated monomer is greater than 50 parts of UV absorber per 100 parts of polymer carrier.

The process for the preparation of a concentrated aqueous polymer dispersion comprises the steps
(i) dissolving, emulsifying or dispersing the oil-soluble organic UV absorber (b) in at least one ethylenically unsaturated monomer (a);
(ii) preparing a conventional o/w emulsion of said UV absorber (b) dissolved, emulsified or dispersed in at least one ethylenically unsaturated monomer (a);
(iii) homogenizing the conventional emulsion to a miniemulsion wherein the droplets of the organic phase have an average diameter below 1000 nm;
(iv) polymerizing the miniemulsion by adding a polymerization initiator;
wherein the weight ratio of oil-soluble organic UV absorber (b) to polymer carrier (a) formed from the ethylenically unsaturated monomer is greater than 50 parts of UV absorber per 100 parts of polymer carrier.

In step ii) preferably a non-ionic, cationic or anionic surfactant is additionally present.

In general anionic and non-ionic surfactants are preferred.
Optionally other water miscible solvents may be present usually less than 10% by weight based on the water content. Exemplary cosolvents useful in the present invention may be selected from the group consisting of aliphatic alcohols, glycols, ethers, glycol ethers, pyrrolidines, N-alkyl pyrrolidinones, N-alkyl pyrrolidones, polyethylene glycols, polypropylene glycols, amides, carboxylic acids and salts thereof, esters, organosulfides, sulfoxides, sulfones, alcohol derivatives, hydroxyether derivatives such as butyl carbitol or cellosolve, amino alcohols, ketones, and the like, as well as derivatives thereof and mixtures thereof. Specific examples include methanol, ethanol, propanol, dioxane, ethylene glycol, propylene glycol, diethylene glycol, glycerol, dipropylene glycol, tetrahydrofurane, and other water-soluble or water-miscible materials, and mixtures thereof.

Preferred are water, water alcohol mixtures, water ethylene glycol or propylene glycol mixtures, water acetone, water tetrahydrofurane, or water dimethylformamide mixtures.

Suitable surfactants or surface active compounds, which may be added are known in the art. The amounts typically used range from 0.01% by weight to 10% by weight, based on the monomer or monomers.

Typical surfactants useful in the present invention are of nonionic, cationic or anionic type.

Examples for anionic surfactants are alkali and ammonium salts of $C_{12}$-$C_{18}$alkyl sulfonic acid, dialkyl esters of succinic acid or sulfuric acid halfesters of ethoxylated alkanoles.

These compounds are known for example from U.S. Pat. No. 4,269,749 and largely items of commerce, such as under the trade name Dowfax® 2A1 (Dow Chemical Company).

Nonionic surfactants are for example aliphatic or aralíphatic compounds such as ethoxylated phenols (mono, di, tri) with an ethoxylation degree of 3 to 50 and alkyl groups in the range from $C_4$-$C_9$, ethoxylated long chain alcohols or polyethyleneoxide/polypropyleneoxide block copolymers.

Furthermore protective colloids such as polyvinylalcohols, starch, cellulose derivatives or copolymers containing vinylpyrrolidone may be added to form a conventional oil in water emulsion according to step b). Further examples are given in "Houben-Weyl, Methoden der Organischen Chemie, Band XIV/1, Makromolekulare Stoffe, G. Thieme Verlag Stuttgart 1961, 411-420".

The homogenization step ii) and iii) is usually carried out by applying mechanical agitation (rotor/stator disperser) followed by using high force dispersion devices like for example a ultrasonic sound equipment (J. Dispersion Sci. Technology 2002, 23(1-3), 333-349) or a high pressure homogenizer (APV Gaulin homogenizer; Microfluidizer) The emulsification/homogenization can be carried out continuously or batchwise. Apparatus for this purpose are known in the art. This is for example described in U.S. Pat. No. 5,108,654.

The polymerization step iv) is carried out by adding a free radical polymerization initiator.

Preferably the free radical initiator is present in an amount of from 0.01 weight-% to 20 weight-%, more preferably from 0.1 weight-% to 10 weight-% and most preferably from 0.2 weight-% to 5 weight-%, based on the monomer or monomer mixture.

The polymerization initiator may be added batchwise or continuously to the reaction mixture.

Preferably the free radical initiator is a bis-azo compound, a peroxide or a hydroperoxide.

Specific preferred radical sources are 2,2'-azobisisobutyronitrile, 2,2'-azobis(2-methyl-butyronitrile), 2,2'-azobis(2,4-dimethylvaleronitrile), 2,2'-azobis(4-methoxy-2,4-dimethylvaleronitrile), 1,1'-azobis(1-cyclohexanecarbonitrile), 2,2'-azobis(isobutyramide) dihydrate, 2-phenylazo-2,4-dimethyl-4-methoxyvaleronitrile, dimethyl-2,2'-azobisisobutyrate, 2-(carbamoylazo)isobutyronitrile, 2,2'-azobis(2,4,4-trimethylpentane), 2,2'-azobis(2-methylpropane), 2,2'-azobis(N,N'-dimethyleneisobutyramidine), free base or hydrochloride, 2,2'-azobis(2-amidino-propane), free base or hydrochloride, 2,2'-azobis{2-methyl-N-[1,1-bis(hydroxymethyl)ethyl]-propionamide} or 2,2'-azobis{2-methyl-N-[1,1-bis(hydroxymethyl)-2-hydroxyethyl]propionamide}; acetyl cyclohexane sulphonyl peroxide, diisopropyl peroxy dicarbonate, t-amyl perneodecanoate, t-butyl perneodecanoate, t-butyl perpivalate, t-amylperpivalate, bis(2,4-dichlorobenzoyl)peroxide, diisononanoyl peroxide, didecanoyl peroxide, dioctanoyl peroxide, dilauroyl peroxide, bis(2-methylbenzoyl)peroxide, disuccinic acid peroxide, diacetyl peroxide, dibenzoyl peroxide, t-butyl per 2-ethylhexanoate, bis-(4-chlorobenzoyl)-peroxide, t-butyl perisobutyrate, t-butyl permaleinate, 1,1-bis(t-butylperoxy)-3,5,5-trimethylcyclohexane, 1,1-bis(t-butylperoxy)cyclohexane, t-butyl peroxy isopropyl carbonate, t-butyl perisononaoate, 2,5-dimethylhexane 2,5-dibenzoate, t-butyl peracetate, t-amyl perbenzoate, t-butyl perbenzoate, 2,2-bis(t-butylperoxy)butane, 2,2 bis(t-butylperoxy)propane, dicumyl peroxide, 2,5-dimethylhexane-2,5-di-t-butylperoxide, 3-t-butylperoxy 3-phenylphthalide, di-t-amyl peroxide, α,α'-bis(t-butylperoxy isopropyl)benzene, 3,5-bis(t-butylperoxy)3,5-dimethyl 1,2-dioxolane, di-t-butyl peroxide, 2,5-dimethylhexyne-2,5-di-t-butylperoxide, 3,3,6,6,9,9-hexa-methyl 1,2,4,5-tetraoxa cyclononane, p-menthane hydroperoxide, pinane hydroperoxide, diisopropylbenzene mono-α-hydroperoxide, cumene hydroperoxide or t-butyl hydroperoxide.

It is also possible to use combinations of Fe-compounds or Co-compounds with peroxo salts or salts of bisulfites or hydrosulfites. These combinations are known as redox systems.

The polymerization temperature depends on the initiator used. Usually the polymerization temperature is in the range of 5° C. to 95° C. and preferably from 30° C. to 90°. If pressure is applied the temperature can rise up to 120° C., however, polymerization under normal pressure is the usual process.

Alternatively the polymerization can be initiated by photoinitiators and electromagnetic radiation, in particular actinic radiation.

Photoinitiators suitable for use in the process according to the invention are in principle any compounds and mixtures that form one or more free radicals when irradiated with electromagnetic waves. These include initiator systems consisting of a plurality of initiators and systems that function independently of one another or synergistically. In addition to coinitiators, for example amines, thiols, borates, enolates, phosphines, carboxylates and imidazoles, it is also possible to use sensitisers, for example acridines, xanthenes, thiazenes, coumarins, thioxanthones, triazines and dyes. A description of such compounds and initiator systems can be found e.g. in Crivello J. V., Dietliker K. K., (1999): Chemistry & Technology of UV & EB Formulation for Coatings, Inks & Paints, and in Bradley G. (ed.) Vol. 3: Photoinitiators for Free Radical and Cationic Polymerisation 2nd Edition, John Wiley & Son Ltd. The photoinitiator suitable for the process according to the invention in step b) may be either an initiator having an unsaturated group or an initiator not having such a group.

Such compounds and derivatives are derived, for example, from the following classes of compounds: benzoins, benzil ketals, acetophenones, hydroxyalkylphenones, aminoalkylphenones, acylphosphine oxides, acylphosphine sulfides, acyloxyiminoketones, alkylamino-substituted ketones, such as Michler's ketone, peroxy compounds, dinitrile compounds, halogenated acetophenones, phenylglyoxylates, dimeric phenylglyoxalates, benzophenones, oximes and oxime esters, thioxanthones, coumarins, ferrocenes, titanocenes, onium salts, sulfonium salts, iodonium salts, diazonium salts, borates, triazines, bisimidazoles, poly-silanes and dyes. It is also possible to use combinations of the compounds from the mentioned classes of compounds with one another and combinations with corresponding coinitiator systems and/or sensitisers.

After the polymerization has been completed, the volatile components, water mainly, can be removed without agglomeration of the particles. The polymer particles can therefore readily be re-dispersed, if desired.

Vaporization of the volatile components can be carried out using standard methods, such as for example spray drying.

The concentrated aqueous polymer dispersion according to the present invention is particularly suitable as UV filters, i.e. for protecting ultraviolet-sensitive organic materials, in particular the skin and hair of humans and animals, from the harmful effects of UV radiation.

These dispersions are therefore suitable as sunscreens in cosmetic, pharmaceutical and veterinary medical preparations.

Another aspect of the present invention is therefore a cosmetic composition, which comprises,
(a) a concentrated aqueous polymer dispersion according to claim 1; and
(b) a cosmetically acceptable carrier.

The cosmetic formulations or pharmaceutical compositions according to the present invention may additionally contain one or more than one further UV filter as listed in Table 2:

TABLE 1

Suitable UV filter substances which can be additionally used with the concentrated aqueous polymer dispersion according to the present invention

| | |
|---|---|
| DE 10013318 | T 1 pp 8-9, all Examples pp 10-13, T 2 pp 13-14, all Examples p 14, Ex A, B, C, D, E, F pp 19-20 |
| DE102004038485A1 | Formula 1 on p 2; Ex 1-4 on p 13; |
| DE102004039281A1 | Formulas I-II on p 1; Ex Ia-Iae on pp 7-12; Ex IIa-IIm on pp 14-15; Ex 1-25 on pp 42-56; |
| DE102005047647 A1 | Formulas I and II on p 3; Ex Ia-Ih on pp 5-7; Ex IIa-IIb on p 7; |
| DE 10206562 A1 | Ex 1-3 p 10, Ex 4-7 p 11, Ex 8-15 pp 12-14 |
| DE 10238144 A1 | Ex on p 3-5; |
| DE 10331804 | T 1 p 4, T 2 + 3 p 5 |
| DE 19704990 A1 | Ex 1-2 on pp 6-7; |
| EP 613 893 | Ex 1-5 + 15, T 1, pp 6-8 |
| EP 0 998 900 A1 | Ex on pp 4-11 |
| EP 1 000 950 | Comp. In Table 1, pp 18-21 |
| EP 1 005 855 | T 3, p 13 |
| EP 1 008 586 | Ex 1-3, pp 13-15 |
| EP 1 008 593 | Ex 1-8, pp 4-5 |
| EP 1 027 883 | Compound VII, p 3 |
| EP 1 027 883 | Comp I-VI, p 3 |
| EP 1 028 120 | Ex 1-5, pp 5-13 |
| EP 1 059 082 | Ex 1; T 1, pp 9-11 |
| EP 1 060 734 | T 1-3, pp 11-14 |
| EP 1 064 922 | Compounds 1-34, pp 6-14 |
| EP 1 077 246 A2 | Ex 1-16 on pp 5-11; |
| EP 1 081 140 | Ex 1-9, pp 11-16 |
| EP 1 103 549 | Compounds 1-76, pp 39-51 |
| EP 1 108 712 | 4,5-Dimorpholino-3-hydroxypyridazine |
| EP 1 123 934 | T 3, p 10 |
| EP 1 129 695 | Ex 1-7, pp 13-14 |
| EP 1142930 A1 | Formulas on p 2; |
| EP 1 167 359 | Ex 1, p 11 and Ex 2, p 12 |
| EP 1 232 148 B1 | Ex 4-17 on pp 3-5; |
| EP 1 258 481 | Ex 1, pp 7,8 |
| EP 1 310 492 A1 | Ex 1-16 on pp 22-30 |
| EP 1 371 654 A1 | Ex on pp 5-7 |
| EP 1 380 583 A2 | Ex 1, p 6; |
| EP 1 423 351 A2 | Ex 1-16 on pp 31-37; |
| EP 1 423 371 A1 | T 1 on pp 4-8, Ex on p 9, Ex 1-9 on pp 36-42; |
| EP 1 454 896 A1 | Ex 1-5 on pp 10-13, Examples on pp 4-5; |
| EP 1 471 059 A1 | Ex 1-5 on pp 4-5; |
| EP 1484051 A2 | Formula III-VII on pp18-19, Ex 7-14 on pp 7-9, Ex 18-23 on pp 11-12, Ex 24-40 on pp 14-17; |
| EP 1648849 A2 | Formula 1 on p 4; Ex 1-2 on pp 13-17; Ex C10 and O10 on pp15-16; |
| EP 1747773 A2 | Formulas I-VI on pp 2-4; Ex I-XXIII on pp 23-26; |
| EP 420 707 B1 | Ex 3, p 13 (CAS Reg. No 80142-49-0) |
| EP 503 338 | T 1, pp 9-10 |
| EP 517 103 | Ex 3, 4, 9, 10 pp 6-7 |
| EP 517 104 | Ex 1, T 1, pp 4-5; Ex 8, T 2, pp 6-8 |
| EP 528 380 A1 | Comp. 1-9 pp 6-9 |
| EP 626 950 | all compounds |
| EP 669 323 | Ex 1-3, p 5 |
| EP 743 309 A1 | Ex 1-12 on pp 18-24; |
| EP 780 382 | Ex 1-11, pp 5-7 |
| EP 823 418 | Ex 1-4, pp 7-8 |
| EP 826 361 | T 1, pp 5-6 |
| EP 832 641 | Ex 5 + 6 p 7; T 2, p 8 |
| EP 832 642 | Ex 22, T 3, pp 10-15; T 4, p 16 |
| EP 848944 A2 | Formulas I and II on p 1; Ex on p 8; Examples on p 10; |
| EP 852 137 | T 2, pp 41-46 |
| EP 858 318 | T 1, p 6 |

TABLE 1-continued

Suitable UV filter substances which can be additionally used with the concentrated aqueous polymer dispersion according to the present invention

| | |
|---|---|
| EP 863 145 | Ex 1-11, pp 12-18 |
| EP 878 469 A1 | T 1, pp 5-7; |
| EP 895 776 | Comp. In rows 48-58, p 3; R 25 + 33, p 5 |
| EP 911 020 | T 2, pp 11-12 |
| EP 916 335 | T 2-4, pp 19-41 |
| EP 924 246 | T 2, p 9 |
| EP 933 376 | Ex 1-15, pp 10-21 |
| EP 944 624 | Ex 1 + 2, pp 13-15 |
| EP 945 125 | T 3 a + b, pp 14-15 |
| EP 95 097 | Ex 1, p 4 |
| EP 967 200 | Ex 2; T 3-5, pp 17-20 |
| EP 969 004 | Ex 5, T 1, pp 6-8 |
| FR 2842806 A1 | Ex I p 10, Ex II p 12 |
| FR 2861075 A1 | Ex 1-3 on pp 12-14; |
| FR 2862641 | Formula 3 on p4; Ex A-J on pp 7-9; |
| FR 2869907 A1 | Formula 1 on p 6; T 1 on p 7-8; Ex 4-39 on pp 12-35; |
| FR 2886143 | Formula 2 on p 4 and 2' on p 5; Ex a-i on pp 7-9; |
| FR 2888113 | Formula 1 on p 2; Ex a-i on pp 3-4; Ex j-n on pp 7-8; |
| FR 2889520 A1 | Formula 4 (Iriflophenone) on p 10; |
| KR 2004025954 | all kojyl benzoate derivatives |
| JP 06135985 A2 | Formula 1 on p 2; Ex 1-8 on pp 7-8; |
| JP 2000319629 | CAS Reg Nos. 80142-49-0, 137215-83-9, 307947-82-6 |
| JP 2003081910 A | Ex on p 1; |
| JP 2005289916 A | Formula I on p 1; Ex Ia-Id on pp 2-3; |
| JP 2005290240 A | Formulas I on p 2, Ex II on p 2; |
| JP 2006131603 | Ex 2 on p 2, Formula 1 on p 2; |
| JP2006-233,181 | Formula 1 on p 2, Ex on p 8; |
| JP 2006335855 | Formula 1-4 on p 2; Ex on p 8; |
| JP 2007131612 | Formula 2 and 3 on p 2, Formula 6-17 pp 9-11; |
| US 2003/0053966A1 | Ex on pp 3-6 |
| US 2004057912 A1 | Ex on p 7-9, Ex 1 on p 10; |
| US 2004057914 A1 | Ex on p 8-12, Ex 1 on p 12; |
| US 2004/0057911A1 | Formula I and II on p 1; formula III and IV on p3; Ex 1-3 on pp 5-6; |
| US 2004/0071640A1 | Ex 1-12 on pp 4-7; |
| US 2004/0091433A1 | Ex 1-6 on pp 14-16; |
| US 2004/0136931A1 | Ex 1-3 on p 7; |
| US 2004/0258636A1 | Ex 1-11 on pp 9-15; |
| US 2005/0019278A1 | Ex 1-9 on pp 6-8; |
| US 2005/0136012A1 | Formula 1 on p 2; |
| US 2005/0136014A1 | Formula a-c on p 2; Examples on p 3; |
| US 2005/0201957A1 | Formula 1 on p1; Ex A, B, C, D, E, F, G on pp 2-3; |
| US 2005/0249681A1 | all compounds on pp 2-3, Ex 1 on p 6; |
| US 2005186157A1 | Formula 1 on p 1; Ex 1-6 on pp 2-4; |
| US 2005260144A1 | Formula I on p1; Formula II on p 3; Ex 1-10 on pp 8-11; |
| US 2006018848A1 | Ex a-p on pp 3-4; |
| US 2006045859A1 | Formula 1 on p 1; Ex 1-10 on pp 2-4; |
| US2006228311 A1 | Formula 1 on p 2, Ex 1 on p 10; |
| US 2007025930A1 | Formula 1 on p1; Ex 1-2 on pp 5-6; |
| U.S. Pat. No. 5,635,343 | all compounds on pp 5-10 |
| U.S. Pat. No. 5,332,568 | Ex 1, p 5, T 1 + 2, pp 6-8 |
| U.S. Pat. No. 5,338,539 | Ex 1-9, pp 3 + 4 |
| U.S. Pat. No. 5,346,691 | Ex 40, p 7; T 5, p 8 |
| U.S. Pat. No. 5,801,244 | Ex 1-5, pp 6-7 |
| U.S. Pat. No. 6,613,340 | Ex I, II pp 9-11, Examples on rows 28-53 p 6 |
| U.S. Pat. No. 6,800,274 B2 | Formulas I-VI and IX-XII on pp 14-18; |
| U.S. Pat. No. 6,890,520 B2 | Ex 1-10 on pp 6-9; |
| U.S. Pat. No. 6,926,887 B2 | Ex A on pp 5/6; Formulas I-VIII on pp 27-29; |
| U.S. Pat. No. 6,936,735 B2 | Formulas 1-2 on p 2; formula 3-4 on p 6; |
| U.S. Pat. No. 6,962,692 B2 | Formulas VII and VIII on p 6; Formulas I, II, IV-VI, IX, X on pp 14-16; Formula III on p 19; |
| U.S. Pat. No. 7,163,673 B2 | Formula III on p 14, Ex 1 on p 7; |
| U.S. Pat. No. 7,217,820 B2 | Formula 1 on p 2, Ex 1 on p 8; |
| U.S. Pat. No. 7,217,821 B2 | Formula 1 on p 2, Ex 1-5 on pp 4-5; |
| WO 0149686 | Ex 1-5, pp 16-21 |
| WO 0168047 | Tables on pp 85-96 |
| WO 0181297 | Ex 1-3, pp 9-11 |
| WO 0191695 | Formula I on p 4, T on p 8 |
| WO 0202501 A1 | Ex Ia-c, p 5 |
| WO 02069926 A1 | Ex on p 9, Ex on pp 17-23 |
| WO 02072583 | T on pp 68-70 |
| WO 02080876 | Ex 1 on pp 7-9 |
| WO 0238537 | All compounds p 3, compounds on rows 1-10 p 4 |
| WO 03004557 A1 | Ex A1-A29 on pp 36-57; |
| WO 03007906 | Ex I-XXIII, pp 42-48 |
| WO 03086340 A1 | Ex B1-B3 on pp 16-17; |
| WO 03086341 A2 | Formula 2-21, pp 4-6; |
| WO 03092643 A1 | T on pp 34-35, compounds listed on p 16 |

TABLE 1-continued

Suitable UV filter substances which can be additionally used with the concentrated aqueous polymer dispersion according to the present invention

| | |
|---|---|
| WO 03097577 A1 | Ex on pp 6-8; Ex 1-3 on pp 15-18; |
| WO 03104183 A1 | Formula I-IV on p 1; Ex 1-5 on pp 27-28; |
| WO 04000256 A1 | Ex 1-10 on pp 18-24 |
| WO 04007592 | Ex 1-9 on pp 18-24; |
| WO 04020398 A1 | Ex 1-3 on pp 14-17 |
| WO 04020398 A1 | Formulas I-VI on pp 21-24, Formula IX on p 25; |
| WO 04075871 | Ex 1-3 on pp 17-18; Ex 7-9 on pp 21-22; |
| WO 05009938 A2 | Formula I on p 1; Ex 1-2 on pp 14-15; |
| WO 05053631 A1 | Ex 1-6 on pp 26-28; |
| WO 05065154 A2 | Formula a-c on pp 5-6; |
| WO 05080341 A1 | Formula 1 on p 3; Examples on pp 9-13; |
| WO 05092282 | Ex 1-9 on pp 34-43; |
| WO 05100319 A1 | Formula I on p 3, Ex 1-22 on p 72-74; |
| WO 05107692 A1 | Formula 1 on p 2; Ex 1-9 on pp 27-29; |
| WO 05118562 A1 | Formula I on p 4; Ex Ia-Ig on p 5; |
| WO 05121108 A1 | Formula I on p 3; Formula Ia on p 5; T 1 on p 7; Ex 3-22 on pp 11-22; |
| WO 06009451 | T 1 on pp 5-8; Formulas III and UV0 on p 9; |
| WO 06016806 | T 1 on pp 6-7; T 2 on p 10; T 3 on p 11; T 4 on p 15; |
| WO 06032741 | Formulas 1-3 on p 1; Ex a-k on pp 5-7; Ex 1-4 on pp 18-20; |
| WO 06048159 | Ex 1-6 on pp 28-34; |
| WO 06064366 A1 | Formula I on p 3; Ex 1c on p 23; Ex 2-9 on pp 24-31; |
| WO 06099952 A2 | Formula on p 4; Ex 3-7 on pp 28-29; |
| WO 06114381 A1 | Formula 1 on p 2; Formula 103 on p 47; |
| WO 06128732 A1 | Formula 1 on p 6, Ex a-i on pp 10-12; |
| WO 06128920 A1 | Formula 1 on p 3; Formulas IA and IB on p 10, Ex 1-15 on pp 21-35; |
| WO 07017179 A1 | Formula I on p 5; Ex 1-5 on pp 52-57; |
| WO 07007283 A1 | Examples on p 13-14; |
| WO 9217461 | Ex 1-22, pp 10-20 |
| WO 9220690 | Polymeric Comp in Examples 3-6 |
| WO 9301164 | T 1 + 2, pp 13-22 |
| WO 9714680 | Ex 1-3, p 10 |
| U.S. Pat. No. 7,229,609 B2 | Comp. A-G pp. 18-20 |
| U.S. Pat. No. 7,229,610 B2 | Comp. A-J pp. 27-30 |
| DE 102005058542 A1 | Comp. Ia-If, pp7-8 |
| JP2007154111 | Compounds according to Formula I, II, III on page 6; Examples on pp 13-18 |
| JP2007112765 | Formula on page 4; Formula on page 8 |
| WO2007081209 | Ex 1-3 on pp 17-18 |
| WO2007060116 | Compounds according to Formula 2 on p 6 with n from 1 to 20 |
| US2007189990 | Ex 2 on p 3 |
| WO2007017179 | Ex 1-5 on pp 52-58 |
| WO2006111233 | Comp. Iah-Iag in the table on pp 10-16 |
| WO2007039110 | Comp. Ia-IIb on pp 7-9 |
| WO2007065524 | Comp. Ia-If on pp 8-9 |
| US2007185057 | Ex 1-10 on pp 10-12 |
| JP2007106701 | Formula II and III on p 2; Formulas on pp 8-11 |
| JP2007153860 | Comp. Ia-Ig and IIa-IIc on p 2. |
| WO2007077729 | Comp. according to Formula I on p 26 with R' = Et and R'' = nBu |
| JP2007204378 | Comp. according to Formula on p 2 with R1 = R2 = OH and R3 = OMe and R4 = H |
| WO2006064366 | Ex 1-9 on pp 21-31 |
| US20070249853 | Ex 1-9 on pp 7-9 |
| US2007224147 | Comp a-k on pp 3-5 |
| JP2007262008 | Formula on p 2 |
| JP2007277209 | Comp Va-c, VIa-c, VIIa-g, VIIIa-g on p 3 |
| WO2006056297 | Ex A p 65 |
| WO2007121818 | Ex 1 on p 54; Ex 2 on p 55; Formulas on pp 56-59 |
| WO2007121845 | Comp. 1-15 on pp 10-13 |
| WO2007144981 | Comp. 1 on p 3 |
| JP2007314501 | Comp. Ia-Ie on p 2; Comp. IIa-IIe on p 2; Cmp. III-VI on p 4; Cmp. VII p 8 |
| WO2007128723 | Comp. Ia-Id on pp 73-74 |
| JP2007261977 | CAS-Reg. Nr. 908576-94-3<br>CAS-Reg. Nr. 941278-56-4 |
| US2007275090 | Ex 1-5 pp 14-17; all compounds on p 9. |
| JP2008007444 | Comp. 2 on p 2; Comp. 6 on p 7; |
| U.S. Pat. No. 7,311,896 | Comp. STR-01-STR13 on p 6 |
| JP2008019229 | Comp. IIa-IIe and IIIa-IIIe on p 2 |
| WO2007137128 | All formulas on pp 10-11 |
| US20080050319 | All formulars p 2 R 43; Ex. 1-9 on pp 9-11 |
| U.S. Pat. No. 7,326,407 | Ex. 1-5 on pp. 10-12. |
| JP2008007443 | Ex. 6 on p 9; Ex. 7 p 10; Ex. 8-25 on pp 10-17 |

TABLE 1-continued

Suitable UV filter substances which can be additionally used with the concentrated aqueous polymer dispersion according to the present invention

| | |
|---|---|
| US200803813 | Comp. Ia-Iz on pp 3-8; comp. Iaa-Iae p 8; comp. IIa-IIm on pp 8-9 |
| EP1894936 | Ex 1 on p 13; Comp. 14 p 17; |
| WO2007006807 | Ex 1-49 on pp 60-90 |
| U.S. Pat. No. 7,354,571 | Comp. a-q on pp 4-7; Ex 1-13 on pp 15-22 |

(Abbreviations T: Table, R: row, Comp: compound, Ex: compound(s) of Patent Example, p: page; the generic scope of the UV absorbers is described in the left-hand column; specific compounds are indicated in the right-hand column)

The cosmetic composition according to the present invention is preferably used for preventing the human hair or skin from the harmful effect of UV radiation.

The cosmetic composition may preferably used in aqueous environment/media/formulation;
for the improvement of the sun protection factor (SPF);
for increasing the amount of UV filters; and
for the improvement of the water resistance.

The cosmetic or pharmaceutical preparations may be, for example, creams, gels, lotions, alcoholic and aqueous/alcoholic solutions, emulsions, wax/fat compositions, stick preparations, powders or ointments. In addition to the above mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of an aqueous polymer dispersion according to the present invention, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or more additional compounds as like fatty alcohols, esters of fatty acids, natural or synthetic triglycerides including glyceryl esters and derivatives, pearlescent waxes, hydrocarbon oils, silicones or siloxanes (organosubstituted polysiloxanes), fluorinated or perfluorinated oils, emulsifiers, adjuvants and additives, super-fatting agents, surfactants, consistency regulators/thickeners and rheology modifiers, polymers, biogenic active ingredients, deodorising active ingredients, anti-dandruff agents, antioxidants, hydrotropic agents, preservatives, bacteria-inhibiting agents, perfume oils, colourants, polymeric beads or hollow spheres as SPF enhancers.

Cosmetic or Pharmaceutical Preparations

Cosmetic or pharmaceutical formulations are contained in a wide variety of cosmetic preparations. There come into consideration, for example, especially the following preparations: skin-care preparations, bath preparations, cosmetic personal care preparations, foot-care preparations, light-protective preparations, skin-tanning preparations, depigmenting preparations, insect-repellents, deodorants, antiperspirants, preparations for cleansing and caring for blemished skin, hair-removal preparations in chemical form (depilation), shaving preparations, fragrance preparations, cosmetic hair-treatment preparations, Presentation Forms The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellent gas or pump-action spray) or an aerosol, in the form of a foam, or in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pre-treatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

Other typical ingredients in such formulations are preservatives, bactericides and bacteriostatic agents, perfumes, dyes, pigments, thickening agents, moisturizing agents, humectants, fats, oils, waxes or other typical ingredients of cosmetic and personal care formulations such as alcohols, poly-alcohols, polymers, electrolytes, organic solvents, silicon derivatives, emollients, emulsifiers or emulsifying surfactants, surfactants, dispersing agents, antioxidants, anti-irritants and anti-inflammatory agents etc.

The cosmetic preparation according to the invention is distinguished by excellent protection of human skin against the damaging effect of sunlight.

The following examples illustrate the invention.

A. PREPARATION EXAMPLES

The following oil-soluble UV absorbers are tested concerning their efficiency in sunscreen products:

| Compound of formula | Structure |
|---|---|
| (101) | [structure: 2-ethylhexyl 4-methoxycinnamate] |
| (102) | [structure: bis-ethylhexyloxyphenol methoxyphenyl triazine] |
| (103) | [structure: benzotriazole with HO, C$_{12}$H$_{25}$, and methyl substituents on phenol ring] |
| (104) | [structure: 4-tert-butyl-4'-methoxydibenzoylmethane] |
| (105) | [structure: 2-ethylhexyl 2-cyano-3,3-diphenylacrylate] |

| Compound of formula | Structure |
|---|---|
| (106) | 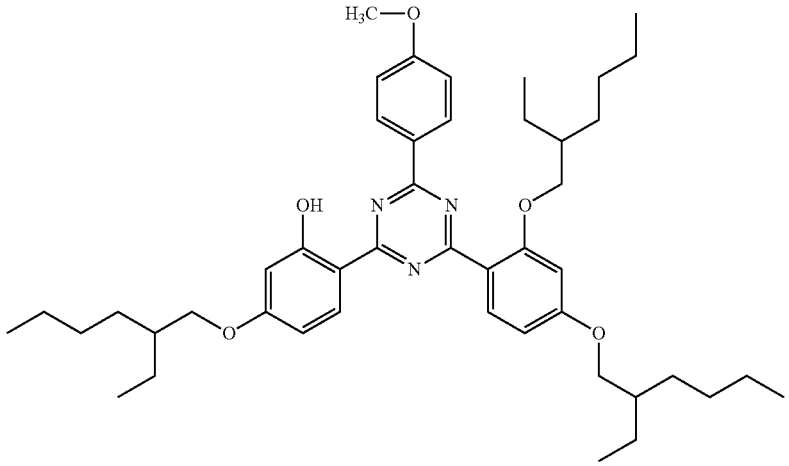 [SMILES: CCCCC(CC)COc1ccc(-c2nc(-c3ccc(OC)cc3)nc(-c3ccc(OCC(CC)CCCC)cc3OCC(CC)CCCC)n2)c(O)c1] |

Example A1

For the preparation of a stable oil/water emulsion a mixture (UV-Mix 1) consisting of
- 65 parts of the compound (101),
- 10 parts of the compound (102) and
- 25 parts of the compound (103)

is dissolved in 20 g methyl methacrylate (MMA), 1.6 g stearyl methacrylate (SMA) and 0.06 g butandioldiacrylate (BDDA). The oil phase is added dropwise to a stirred solution of 1.6 g sodium dodecylsulphate in 56.5 g deionised water. After stirring for 30 min and ultrasonically converting a kinetically stable emulsion is obtained with an average droplet size below 250 nm. The emulsion is heated up to 55° C. and the redox initiator (0.06 g ascorbic acid dissolved in 3 g deionised water; 0.25 ml $H_2O_2$ (35%) diluted in 0.5 g deionised water) is subsequently added to the reaction mixture.

The reaction mixture is continuously stirred by a mechanical stirrer and is maintained at 55° C. for three hours, then cooled to room temperature (RT) and filtered via a 20 μm filter.

The resulting particle size $D_{INT}$ is 141 nm.

The active content of the oil soluble UV absorber mixture of the compounds (101), (102) and (103) is 20 wt %, based on the total weight of the emulsion.

Example A2

For the preparation of a stable oil/water emulsion a mixture (UV-Mix 1) consisting of
- 65 parts of the compound (101),
- 10 parts of the compound (102) and
- 25 parts of the compound (103)

is dissolved in 16 g methyl methacrylate (MMA), 1.6 g stearyl methacrylate (SMA) and 0.05 g butandioldiacrylate (BDDA). The oil phase is added dropwise to a stirred solution of 1.6 g sodium dodecylsulphate in 56.5 g deionised water. After stirring for 30 min and ultrasonically converting a kinetically stable emulsion is obtained with an average droplet size below 250 nm. The emulsion is heated up to 55° C. and the redox initiator (0.08 g ascorbic acid dissolved in 3 g deionised water; 0.32 ml $H_2O_2$ (35%) diluted in 0.5 g deionised water) is subsequently added to the reaction mixture.

The reaction mixture is continuously stirred by a mechanical stirrer and is maintained at 55° C. for three hours, then cooled to RT and filtered via a 20 μm filter. The resulting particle size $D_{INT}$ is 182 nm.

The active content of the oil soluble UV absorber mixture of the compounds (101), (102) and (103) is 24 wt %, based on the total weight of the emulsion.

Example A3

For the preparation of a stable oil/water emulsion a mixture (UV-Mix 1) consisting of
- 65 parts of the compound (101),
- 10 parts of the compound (102) and
- 25 parts of the compound (103)

is dissolved in 20 g ethyl acrylate (EA), 1.6 g stearyl methacrylate (SMA) and 0.06 g butandioldiacrylate (BDDA).

The oil phase is added dropwise to a stirred solution of 1.6 g sodium dodecylsulphate in 56.5 g deionised water.

After stirring for 30 min and ultrasonically converting a kinetically stable emulsion is obtained with an average droplet size below 250 nm. The emulsion is heated up to 55 C and the redox initiator (0.06 g ascorbic acid dissolved in 3 g deionised water; 0.25 ml $H_2O_2$ (35%) diluted in 0.5 g deionised water) is subsequently added to the reaction mixture.

The reaction mixture is continuously stirred by a mechanical stirrer and is maintained at 55° C. for three hours, then cooled to RT and filtered via a 20 μm filter. The resulting particle size $D_{INT}$ is 156 nm.

The active content of the oil soluble UV absorber mixture of the compounds (101), (102) and (103) is 20 wt %, based on the total weight of the emulsion.

Example A4

For the preparation of a stable oil/water a mixture (UV-Mix 1) consisting of
- 65 parts of the compound (101),
- 10 parts of the compound (102) and
- 25 parts of the compound (103)

is dissolved in 16 g ethyl acrylate (EA), 1.6 g stearyl methacrylate (SMA) and 0.05 g butandioldiacrylate (BDDA). The oil phase is added dropwise to a stirred solution of 1.6 g sodium dodecylsulphate in 56.5 g deionised water. After stirring for 30 min and ultrasonically converting a kinetically stable emulsion is obtained with an average droplet size below 250 nm. The emulsion is heated up to 55° C. and the redox initiator (0.08 g ascorbic acid dissolved in 3 g deionised water; 0.32 ml $H_2O_2$ (35%) diluted in 0.5 g deionised water) is subsequently added to the reaction mixture. The reaction mixture is continuously stirred by a mechanical stirrer and is maintained at 55° C. for three hours, then cooled to RT and filtered via a 20 μm filter.

The resulting particle size $D_{INT}$ is 199 nm.

The active content of the oil soluble UV absorber mixture of the compounds (101), (102) and (103) is 24 wt %, based on the total weight of the emulsion.

Example A5

For the preparation of a stable oil/water emulsion a mixture (UV-Mix 1) consisting of
- 65 parts of the compound (101),
- 10 parts of the compound (102) and
- 25 parts of the compound (103)

Is dissolved in 40 g methyl methacrylate (MMA), 4.8 g stearyl methacrylate (SMA) and 0.12 g butandioldiacrylate (BDDA). The oil phase is added dropwise to a stirred solution of 10.3 g Disponil® FES 32 IS (31 wt % active, Cognis Deutschland GmbH&Co.KG) in 115 g deionised water. After stirring for 30 min and ultrasonically converting a kinetically stable emulsion is obtained with an average droplet size below 250 nm.

The emulsion is heated up to 55° C. and the redox initiator (0.2 g ascorbic acid dissolved in 3 g deionised water; 0.81 ml $H_2O_2$ (35%) diluted in 2.0 g deionised water) is subsequently added to the reaction mixture. The reaction mixture is continuously stirred by a mechanical stirrer and is maintained at 55° C. for three hours, then cooled to RT and filtered via a 20 μm filter.

The resulting particle size $D_{INT}$ is 170 nm.

The active content of the oil soluble UV absorber mixture of the compounds (101), (102) and (103) is 20 wt %, based on the total weight of the emulsion.

Example A6

The following samples were prepared with a monomer mixture (Mix I), containing 11% hydroxyethyl methacrylate, 15% vinyl toluol, 15% cyclohexyl methacrylate, 28% methyl methacrylate and 31% iso-butyl methacrylate.

For the preparation of a stable oil/water emulsion a mixture (UV-Mix1) consisting of
- 65 parts of the compound (101),
- 10 parts of the compound (102) and
- 25 parts of the compound (103)

Is dissolved in 40 g of Mix I, 3.2 g stearyl methacrylate (SMA) and 0.12 g butandioldiacrylate (BDDA). The oil phase is added dropwise to a stirred solution of 10.3 g Disponil® FES 32 IS (31 wt % active, Cognis Deutschland GmbH&Co.KG) in 110 g deionised water. After stirring for 30 min and ultrasonically converting a kinetically stable emulsion is obtained with an average droplet size below 250 nm. The emulsion is heated up to 55° C. and the redox initiator (0.2 g ascorbic acid dissolved in 5 g deionised water; 0.81 ml $H_2O_2$ (35%) diluted in 5.0 g deionised water) is subsequently added to the reaction mixture. The reaction mixture is continuously stirred by a mechanical stirrer and is maintained at 55° C. for three hours, then cooled to RT and filtered via a 20 μm filter. The resulting particle size $D_{INT}$ is 198 nm. The final active content of the oil soluble UV absorber mixture of the compounds (101), (102) and (103) is 20 wt %, based on the total weight of the emulsion.

Example A7

For the preparation of a stable oil/water emulsion a mixture (UV-Mix1) consisting of
- 65 parts of the compound (101),
- 10 parts of the compound (102) and
- 25 parts of the compound (103)

Is dissolved in 40 g of Mix I and 3.2 g stearyl methacrylate (SMA). The oil phase is added dropwise to a stirred solution of 10.3 g Disponil® FES 32 IS (31 wt % active, Cognis Deutschland GmbH&Co.KG) in 110 g deionised water. After stirring for 30 min and ultrasonically converting a kinetically stable emulsion is obtained with an average droplet size below 250 nm. The emulsion is heated up to 55° C. and the redox initiator (0.2 g ascorbic acid dissolved in 5 g deionised water; 0.81 ml $H_2O_2$ (35%) diluted in 5.0 g deionised water) is subsequently added to the reaction mixture. The reaction mixture is continuously stirred by a mechanical stirrer and is maintained at 55° C. for three hours, then cooled to RT and filtered via a 20 μm filter. The resulting particle size $D_{INT}$ is 198 nm.

The final active content of the oil soluble UV absorber mixture of the compounds (101), (102) and (103) is 20 wt %, based on the total weight of the emulsion.

Example A8

For the preparation of a stable oil/water emulsion a mixture (UV-Mix1) consisting of
- 65 parts of the compound (101),
- 10 parts of the compound (102) and
- 25 parts of the compound (103)

is dissolved in 40 g of Mix I, 3.2 g stearyl methacrylate (SMA) and 0.06 g dodecyl mercaptane (DDM). The oil phase is added dropwise to a stirred solution of 10.3 g Disponil® FES 32 IS (31 wt % active, Cognis Deutschland GmbH&Co.KG) in 110 g deionised water. After stirring for 30 min and ultrasonically converting a kinetically stable emulsion is obtained with an average droplet size below 250 nm. The emulsion is heated up to 55° C. and the redox initiator (0.2 g ascorbic acid dissolved in 5 g deionised water; 0.81 ml $H_2O_2$ (35%) diluted in 5.0 g deionised water) is subsequently added to the reaction mixture.

The reaction mixture is continuously stirred by a mechanical stirrer and is maintained at 55° C. for three hours, then cooled to RT and filtered via a 20 μm filter.

The resulting particle size $D_{INT}$ is 198 nm.

The final active content of the oil soluble UV absorber mixture of the compounds (101), (102) and (103) is 20 wt %, based on the total weight of the emulsion.

In analogy to examples A1 to A8 the following oil soluble UV filters or mixtures of oil soluble UV filters are used for the preparation of stable emulsions as described above:

| Example A9 to A16: | Example A17 to A24: |
|---|---|
| A mixture (UV-Mix2) consisting of 97 parts of the compound (101), 1 part of the compound (102) and 2 parts of the compound (103) | A mixture (UV-Mix3) consisting of 90 parts of the compound (101) and 10 parts of the compound (102) |
| Example A25 to A32: | Example A33 to A40: |
| Compound (101) | Compound (102) |
| Example A41 to A48: | Example A49 to A56: |
| A mixture (UV-Mix4) consisting of 33.3 parts of the compound (104), 66.6 parts of the compound (105) | A mixture (UV-Mix5) consisting of 30 parts of the compound (104), 70 parts of the compound (105) |
| Examples A57 to A64: | Examples A 65 to A72: |
| A mixture (UV-Mix6) consisting of 90 parts of the compound (102), 10 parts of the compound (106) | A mixture (UV-Mix7) consisting of 99 parts of the compound (102), 1 part of the compound (106) |
| Examples A73 to A80: | Examples A81 to A88: |
| A mixture (UV-Mix8) consisting of 80 parts of the compound (102), 20 parts of the compound (103) | A mixture (UV-Mix9) consisting of 77 parts of the compound (102), 33 parts of the compound (103) |
| Examples A89 to A96: | |
| A mixture (UV-Mix10) consisting of 75 parts of the compound (102), 20 parts of the compound (103) 5 parts of the compound (106) | |

In analogy to examples A1 to A104 the above mentioned oil soluble UV filters [compound (101) to (106)] as well as their mixtures [(UV-Mix 1) to (UV-Mix10)] can be used for the preparation of stable emulsions as described in the following preparation examples:

Example A97 to A112

For the preparation of a stable oil/water emulsion an oil soluble UV filter selected from [compound (101) to (106)]

or a mixture of oil soluble UV filters selected from [(UV-Mix 1) to (UV-Mix10)]

is dissolved in 34.2 g of methyl methacrylate (MMA), 3.04 g stearyl methacrylate (SMA), 0.76 g methyl acrylic acid (MAA) and 0.11 g butandiol diacrylate (BDDA). The oil phase is added dropwise to a stirred solution of 10.3 g Disponil® FES 32 IS (31 wt % active, Cognis Deutschland GmbH&Co.KG) in 110 g deionised water. After stirring for 30 min and ultrasonically converting a kinetically stable emulsion is obtained with an average droplet size below 250 nm. The emulsion is heated up to 55° C. and the redox initiator (0.2 g ascorbic acid dissolved in 5 g deionised water; 0.81 ml $H_2O_2$ (35%) diluted in 5.0 g deionised water) is subsequently added to the reaction mixture.

The reaction mixture is continuously stirred by a mechanical stirrer and is maintained at 55° C. for three hours, then cooled to RT and filtered via a 20 µm filter.

The resulting particle size $D_{INT}$ is 198 nm.

The final active content of the oil soluble UV absorber is 20 wt %, based on the total weight of the emulsion.

Example A113 to A128

For the preparation of a stable oil/water emulsion an oil soluble UV filter selected from [compound (101) to (106)]

or a mixture of oil soluble UV filters selected from [(UV-Mix 1) to (UV-Mix10)]

is dissolved in 76 g of methyl methacrylate (MMA) and 0.11 g butandiol diacrylate (BDDA). The oil phase is added dropwise to a stirred solution of 10.3 g Disponil® FES 32 IS (31 wt % active, Cognis Deutschland GmbH&Co.KG) in 110 g deionised water. After stirring for 30 min and ultrasonically converting a kinetically stable emulsion is obtained with an average droplet size below 250 nm. The emulsion is heated up to 55° C. and the redox initiator (0.2 g ascorbic acid dissolved in 5 g deionised water; 0.81 ml $H_2O_2$ (35%) diluted in 5.0 g deionised water) is subsequently added to the reaction mixture.

The reaction mixture is continuously stirred by a mechanical stirrer and is maintained at 55° C. for three hours, then cooled to RT and filtered via a 20 µm filter.

The resulting particle size $D_{INT}$ is 198 nm.

The final active content of the oil soluble UV absorber is 20 wt %, based on the total weight of the emulsion.

Example A129 to A144

For the preparation of a stable oil/water emulsion an oil soluble UV filter selected from [compound (101) to (106)]

or a mixture of oil soluble UV filters selected from [(UV-Mix 1) to (UV-Mix10)]

is dissolved in 76 g of methyl methacrylate (MMA) and 1.14 g butandiol diacrylate (BDDA). The oil phase is added dropwise to a stirred solution of 10.3 g Disponil® FES 32 IS (31 wt % active, Cognis Deutschland GmbH&Co.KG) in 110 g deionised water. After stirring for 30 min and ultrasonically converting a kinetically stable emulsion is obtained with an average droplet size below 250 nm. The emulsion is heated up to 55° C. and the redox initiator (0.2 g ascorbic acid dissolved in 5 g deionised water; 0.81 ml $H_2O_2$ (35%) diluted in 5.0 g deionised water) is subsequently added to the reaction mixture.

The reaction mixture is continuously stirred by a mechanical stirrer and is maintained at 55° C. for three hours, then cooled to RT and filtered via a 20 µm filter.

The resulting particle size $D_{INT}$ is 198 nm.

The final active content of the oil soluble UV absorber is 20 wt %, based on the total weight of the emulsion.

Example A145 to A160 or the preparation of a stable oil/water emulsion an oil soluble UV filter selected from [compound (101) to (106)]

or a mixture of oil soluble UV filters selected from [(UV-Mix 1) to (UV-Mix10)]

is dissolved in 76 g of methyl methacrylate (MMA) and 1.14 g trimethylolpropane triacrylate (TMPTA). The oil phase is added dropwise to a stirred solution of 10.3 g Disponil® FES 32 IS (31 wt % active, Cognis Deutschland GmbH&Co.KG) in 110 g deionised water. After stirring for 30 min and ultrasonically converting a kinetically stable emulsion is obtained with an average droplet size below 250 nm. The emulsion is heated up to 55° C. and the redox initiator (0.2 g ascorbic acid dissolved in 5 g deionised water; 0.81 ml $H_2O_2$ (35%) diluted in 5.0 g deionised water) is subsequently added to the reaction mixture.

The reaction mixture is continuously stirred by a mechanical stirrer and is maintained at 55° C. for three hours, then cooled to RT and filtered via a 20 μm filter.

The resulting particle size $D_{INT}$ is 198 nm.

The final active content of the oil soluble UV absorber is 20 wt %, based on the total weight of the emulsion.

B. APPLICATION EXAMPLES

The UV absorbing PMMA polymerisates are incorporated under stirring in the aqueous phase of cosmetic formulations:

Basis Formulation 1:
SPF8 (5% OCR; 0.9% BMDBM, 0.8% Tinosorb S)

| | INCI-Name | % w/w (as supplied) |
|---|---|---|
| Part A | Butylene Glycol Dicaprylate/Dicaprate | 8.00 |
| | Dicaprylyl Ether | 6.00 |
| | Octyldodecanol | 5.00 |
| | Cyclomethicone | 3.00 |
| | Glyceryl Stearate Citrate | 2.50 |
| | Stearyl Alcohol | 2.30 |
| | Butyl Methoxydibenzoylmethane | 0.90 |
| | Bis-Ethylhexyloxyphenol Methoxyphenyl Triazine | 0.80 |
| | Hydrogenated Coco-Glycerides | 1.50 |
| | Octocrylene | 5.00 |
| | PVP/Hexadecene Copolymer | 0.80 |
| Part B | Aqua | Qs to 100 |
| | Glycerin | 7.00 |
| | Xanthan Gum | 0.10 |
| | Acrylates/C10-30 Alkyl Acrylate Crosspolymer | 0.05 |
| | Disodium EDTA | 0.05 |
| Part C | DMDM Hydantoin | 0.30 |
| | Phenoxyethanol | 0.70 |

| Example B1: | Addition of 10% PMMA polymerisate according to Preparation Example A1 in the water phase of base formation 1 |
|---|---|
| Example B2: | Addition of 1.3% Ethylhexyl Methoxycinnnamate, 0.5% Benzotriazolyl Dodecyl p-Cresol and 0.2% Bis-Ethylhexyloxyphenol Methoxyphenyl Triazine in the oil phase of the Base formulation 1 as comparative example |
| Example B3: | Base formulation 1 without further additives as reference example |

The additions from base Formulation 1 are incorporated in the base formulation 1 at 30 to 40° C. with stirring.

The samples are applied on sand blasted PMMA plates (delivered by Helioscience, Marseille, France) with a concentration of 1.4 mg/cm$^2$, irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper12.

| Results | | | |
|---|---|---|---|
| | Example B1 | Example B2 | Example B3 |
| In vitro SPF | 6.3 | 5.0 | 3.3 |

Basis Formulation 2:
O/W anionic SPF10 (5% OCR; 2.5% BMDBM, 1.7% Tinosorb S)

| | INCI-Name | % w/w (as supplied) |
|---|---|---|
| Part A | Phenethyl Benzoate | 5.50 |
| | Cetearyl Ethylhexanoate | 4.00 |
| | Glyceryl Stearate | 4.00 |
| | Cetearyl Alcohol (and) PEG-20 Stearate | 2.50 |
| | Potassium Cetyl Phosphate | 2.00 |
| | Butyl Methoxydibenzoylmethane | 2.50 |
| | Octocrylene | 5.00 |
| | Bis-Ethylhexyloxyphenol Methoxyphenyl Triazine | 1.70 |
| Part B | Aqua | Qs to 100 |
| | Propylene Glycol | 3.50 |
| | Sodium EDTA | 0.20 |
| | Xanthan Gum | 0.15 |
| Part C | Propylene Glycol (and) Diazolidinyl Urea (and) Methylparaben (and) Propylparaben | 0.70 |
| Part D | Triethanolamine | qs |

| Example B4: | Addition of 10% PMMA polymerisate according to Preparation Example A1 in the water phase of base formation 2 |
|---|---|
| Example B5: | Addition of 1.3% Ethylhexyl Methoxycinnnamate, 0.5% Benzotriazolyl Dodecyl p-Cresol and 0.2% Bis-Ethylhexyloxyphenol Methoxyphenyl Triazine in the oil phase of the Base formulation 2 as comparative example |
| Example B6: | Base formulation 2 without further additives as reference example |

The components of B4, B5 and B6 respectively are incorporated in the base formulation 2 at 50 to 60° C. with stirring.

The samples are applied on sand blasted PMMA plates (delivered by Helioscience, Marseille, France) with a concentration of 1.4 mg/cm$^2$, irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper12.

| Results | | | |
|---|---|---|---|
| | Example B4 | Example B5 | Example B6 |
| In vitro SPF | 12.4 | 11.7 | 8.4 |

Basis Formulation 3:

O/W anionic SPF25 (10% OCR; 2.6% BMDBM, 2.5% Tinosorb S, 1.6% TiO$_2$)

|  | INCI-Name | % w/w (as supplied) |
|---|---|---|
| Part A | Phenethyl Benzoate | 6.00 |
|  | Cetearyl Ethylhexanoate | 2.00 |
|  | Glyceryl Stearate | 4.00 |
|  | Cetearyl Alcohol (and) PEG-20 Stearate | 3.00 |
|  | Potassium Cetyl Phosphate | 2.00 |
|  | Butyl Methoxydibenzoylmethane | 2.60 |
|  | Octocrylene | 10.00 |
|  | Bis-Ethylhexyloxyphenol Methoxyphenyl Triazine | 2.50 |
|  | Titanium Dioxide (and) Aluminum Hydroxide (and) Stearic Acid | 1.60 |
| Part B | Aqua | Qs to 100 |
|  | Propylene Glycol | 3.50 |
|  | Sodium EDTA | 0.20 |
|  | Xanthan Gum | 0.15 |
| Part C | Propylene Glycol (and) Diazolidinyl Urea (and) Methylparaben (and) Propylparaben | 0.70 |
| Part D | Triethanolamine | qs |

| Example B7: | Addition of 10% PMMA polymerisate according to Preparation Example A1 in the water phase of base formation 3 |
|---|---|
| Example B8: | Addition of 1.3% Ethylhexyl Methoxycinnamate, 0.5% Benzotriazolyl Dodecyl p-Cresol and 0.2% Bis-Ethylhexyloxyphenol Methoxyphenyl Triazine in the oil phase of the Base formulation 3 as comparative example |
| Example B9: | Base formulation 3 without further additives as reference example |

The components of B7, B85 and B9 respectively are incorporated in the base formulation 3 at 50 to 60° C. with stirring.

The samples are applied on sand blasted PMMA plates (delivered by Helioscience, Marseille, France) with a concentration of 1.4 mg/cm$^2$, irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper12.

| Results | | | |
|---|---|---|---|
|  | Example B7 | Example B8 | Example B9 |
| In vitro SPF | 27 | 25 | 18 |

The in-vitro SPF Very Water Resistance (VWR) Evaluations Were Conducted Using VITRO-SKIN® N-19 as the Substrate According to the IMS, Inc. in vitro Very Water Resistant Test Protocol.

| Results | | |
|---|---|---|
|  | Example B7 | Example B8 |
| % SPF remainingg | 98 | 87 |

Basis Formulation 4:

W/O SPF10 (5% OCR; 2.5% BMDBM, 1.7% Tinosorb S)

|  | INCI-Name | % w/w (as supplied) |
|---|---|---|
| Part A | Phenethyl Benzoate | 7.00 |
|  | Microcrystalline Wax | 1.50 |
|  | Mineral Oil | 3.50 |
|  | Isohexadecane | 3.50 |
|  | Bis-Ethylhexyloxyphenol Methoxyphenyl Triazine | 1.70 |
|  | Octocrylene | 5.00 |
|  | Cetyl Alcohol | 0.50 |
|  | Butyl Methoxydibenzoylmethane | 2.50 |
|  | Hydrogenated Castor Oil | 0.80 |
|  | PEG-30 Dipolyhydroxystearate | 3.50 |
|  | PEG-22/Dodecyl Glycol Copolymer | 1.50 |
| Part B | Aqua | Qs to 100 |
|  | Propylene Glycol | 4.00 |
|  | Hydrated Magnesium Sulfate | 0.70 |
|  | Sodium EDTA | 0.20 |
|  | Glycerin | 2.00 |
| Part C | Diazolidinyl Urea (and) Methyl paraben (and) Propyl paraben (and) Propylene Glycol | 0.50 |

| Example B10: | Addition of 10% PMMA polymerisate according to Preparation Example A1 in the water phase of base formation 4 |
|---|---|
| Example B11: | Addition of 1.3% Ethylhexyl Methoxycinnnamate, 0.5% Benzotriazolyl Dodecyl p-Cresol and 0.2% Bis-Ethylhexyloxyphenol Methoxyphenyl Triazine in the oil phase of the Base formulation 4 as comparative example |
| Example B12: | Base formulation 4 without further additives as reference example |

The components of B10, B11 and B12 respectively are incorporated in the base formulation 4 at 50 to 60° C. with stirring.

The samples are applied on sand blasted PMMA plates (delivered by Helioscience, Marseille, France) with a concentration of 1.4 mg/cm$^2$, irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper12.

| Results | | | |
|---|---|---|---|
|  | Example B10 | Example B11 | Example B12 |
| In vitro SPF | 19 | 17 | 11 |

Basis Formulation 5:

W/O SPF25 (10% OCR; 2.6% BMDBM, 2.5% Tinosorb S, 1.6% TiO$_2$)

|  | INCI-Name | % w/w (as supplied) |
|---|---|---|
| Part A | Phenethyl Benzoate | 5.00 |
|  | Microcrystalline Wax | 1.50 |
|  | Mineral Oil | 3.50 |
|  | Isohexadecane | 3.50 |
|  | Bis-Ethylhexyloxyphenol Methoxyphenyl Triazine | 2.50 |
|  | Octocrylene | 10.00 |
|  | Cetyl Alcohol | 1.50 |

|  | INCI-Name | % w/w (as supplied) |
|---|---|---|
|  | Butyl Methoxydibenzoylmethane | 2.60 |
|  | Titanium Dioxide (and) Stearic Acid (and) Alumina | 1.60 |
|  | Hydrogenated Castor Oil | 1.00 |
|  | PEG-30 Dipolyhydroxystearate | 3.50 |
|  | PEG-22/Dodecyl Glycol Copolymer | 1.80 |
| Part B | Aqua | Qs to 100 |
|  | Propylene Glycol | 4.00 |
|  | Hydrated Magnesium Sulfate | 0.70 |
|  | Sodium EDTA | 0.20 |
|  | Glycerin | 2.00 |
| Part C | Diazolidinyl Urea (and) Methyl paraben (and) Propyl paraben (and) Propylene Glycol | 0.50 |

| Example B13: | Addition of 10% PMMA polymerisate according to Preparation Example A1 in the water phase of base formation 5 |
|---|---|
| Example B14: | Addition of 1.3% Ethylhexyl Methoxycinnnamate, 0.5% Benzotriazolyl Dodecyl p-Cresol and 0.2% Bis-Ethylhexyloxyphenol Methoxyphenyl Triazine in the oil phase of the Base formulation 5 as comparative example |
| Example B15: | Base formulation 5 without further additives as reference example |

The components of B13, B14 and B15 respectively are incorporated in the base formulation 5 at 50 to 60° C. with stirring.

The samples are applied on sand blasted PMMA plates (delivered by Helioscience, Marseille, France) with a concentration of 1.4 mg/cm², irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper12.

| Results | | | |
|---|---|---|---|
|  | Example B13 | Example B14 | Example B15 |
| In vitro SPF | 49 | 30 | 36 |

The samples were tested in vivo according to the International Sun Protection Factor (SPF) Test Method, COLIPA, May 2006 (screening) and Colipa Recommendation No. 11—SPF Classification/upper limit, COLIPA, June 2002.

| Results | | |
|---|---|---|
|  | Example B13 | Example B14 |
| In vivo SPF | 47.7 | 32.5 |

Basis Formulation 6:
O/W non-ionic SPF10 (5% OCR; 2.5% BMDBM, 1.7% Tinosorb S)

|  | INCI-Name | % w/w (as supplied) |
|---|---|---|
| Part A | Polyglyceryl-3 Methylglucose Distearate | 2.00 |
|  | Steareth-2 | 2.50 |
|  | Steareth-21 | 1.00 |
|  | Caprylic/Capric Triglyceride | 6.50 |
|  | Isopropyl Palmitate | 5.80 |
|  | Decyl Oleate | 5.70 |
|  | Cetyl Alcohol | 0.70 |
|  | Butyl Methoxydibenzoylmethane | 2.50 |
|  | Octocrylene | 5.00 |
|  | Bis-Ethylhexyloxyphenol Methoxyphenyl Triazine | 1.70 |
| Part B | Aqua | Qs to 100 |
|  | Glycerin | 3.00 |
|  | Disodium EDTA | 0.20 |
|  | Xanthan Gum | 0.30 |
| Part C | Phenoxyethanol (and) Methylparaben (and) Ethylparaben (and) Butylparaben (and) Propylparaben (and) Isobutylparaben | 1.00 |
| Part D | Water (and) Sodium Hydroxide | qs |

| Example B16: | Addition of 10% PMMA polymerisate according to Preparation Example A1 in the water phase of base formation 6 |
|---|---|
| Example B17: | Addition of 1.3% Ethylhexyl Methoxycinnnamate, 0.5% Benzotriazolyl Dodecyl p-Cresol and 0.2% Bis-Ethylhexyloxyphenol Methoxyphenyl Triazine in the oil phase of the Base formulation 6 as comparative example |
| Example B18: | Base formulation 6 without further additives as reference example |

The components of B16, B17 and B18 respectively are incorporated in the base formulation 6 at 50 to 60° C. with stirring.

The samples are applied on sand blasted PMMA plates (delivered by Helioscience, Marseille, France) with a concentration of 1.4 mg/cm², irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper12.

| Results | | | |
|---|---|---|---|
|  | Example B16 | Example B17 | Example B18 |
| In vitro SPF | 18.5 | 14.0 | 11.7 |

Basis Formulation 7:
O/W non-ionic SPF25 (10% OCR; 2.6% BMDBM, 2.5% Tinosorb S, 1.6% TiO$_2$)

|  | INCI-Name | % w/w (as supplied) |
|---|---|---|
| Part A | Polyglyceryl-3 Methylglucose Distearate | 2.00 |
|  | Steareth-2 | 2.50 |
|  | Steareth-21 | 1.00 |
|  | Caprylic/Capric Triglyceride | 6.50 |
|  | Isopropyl Palmitate | 5.80 |
|  | Decyl Oleate | 5.70 |
|  | Cetyl Alcohol | 1.50 |
|  | Butyl Methoxydibenzoylmethane | 2.60 |
|  | Octocrylene | 10.00 |

-continued

| | INCI-Name | % w/w (as supplied) |
|---|---|---|
| | Bis-Ethylhexyloxyphenol Methoxyphenyl Triazine | 2.50 |
| | Titanium Dioxide (and) Stearic Acid (and) Alumina | 1.60 |
| Part B | Aqua | Qs to 100 |
| | Glycerin | 3.00 |
| | Disodium EDTA | 0.20 |
| | Xanthan Gum | 0.30 |
| Part C | Phenoxyethanol (and) Methylparaben (and) Ethylparaben (and) Butylparaben (and) Propylparaben (and) Isobutylparaben | 1.00 |
| Part D | Water (and) Sodium Hydroxide | qs |

| Example B19: | Addition of 10% PMMA polymerisate according to Preparation Example A1 in the water phase of base formation 7 |
|---|---|
| Example B20: | Addition of 1.3% Ethylhexyl Methoxycinnnamate, 0.5% Benzotriazolyl Dodecyl p-Cresol and 0.2% Bis-Ethylhexyloxyphenol Methoxyphenyl Triazine in the oil phase of the Base formulation 7 as comparative example |
| Example B21: | Base formulation 7 without further additives as reference example |

The components of B19, B20 and B21 respectively are incorporated in the base formulation 7 at 50 to 60° C. with stirring.

The samples are applied on sand blasted PMMA plates (delivered by Helioscience, Marseille, France) with a concentration of 1.4 mg/cm$^2$, irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper12.

| Results | | | |
|---|---|---|---|
| | Example B19 | Example B20 | Example B21 |
| In vitro SPF | 33.0 | 27.5 | 25.4 |

Basis Formulation 8:
O/W gel SPF10 (5% OCR; 2.5% BMDBM, 1.7% Tinosorb S)

| | INCI-Name | % w/w (as supplied) |
|---|---|---|
| Part A | Stearyl Dimethicone | 6.00 |
| | Octyldodecanol | 4.00 |
| | C12-15 Alkyl Benzoate | 13.80 |
| | Octocrylene | 5.00 |
| | Butyl Methoxydibenzoylmethane | 2.50 |
| | Bis-Ethylhexyloxyphenol Methoxyphenyl Triazine | 1.70 |
| Part B | Aqua | Qs to 100 |
| | Acrylates/C10-30 Alkyl Acrylate Crosspolymer | 0.35 |
| | Glycerin | 6.00 |
| | Disodium EDTA | 0.10 |
| Part C | Tocopheryl Acetate | 0.50 |
| | Phenoxyethanol (and) Methylparaben (and) Ethylparaben (and) Butylparaben (and) Propylparaben (and) Isobutylparaben | 1.00 |

| Example B22: | Addition of 10% PMMA polymerisate according to Preparation Example A1 in the water phase of base formation 8 |
|---|---|
| Example B23: | Addition of 1.3% Ethylhexyl Methoxycinnnamate. 0.5% Benzotriazolyl Dodecyl p-Cresol and 0.2% Bis-Ethylhexyloxyphenol Methoxyphenyl Triazine in the oil phase of the Base formulation 8 as comparative example |
| Example B24: | Base formulation 8 without further additives as reference example |

The components of B22, B23 and B24 respectively are incorporated in the base formulation 8 at 50 to 60° C. with stirring.

The samples are applied on sand blasted PMMA plates (delivered by Helioscience, Marseille, France) with a concentration of 1.4 mg/cm$^2$, irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper12.

| Results | | | |
|---|---|---|---|
| | Example B22 | Example B23 | Example B24 |
| In vitro SPF | 14.5 | 11.2 | 8.6 |

Basis Formulation 9: Water/Silicon

| | INCI-Name | % w/w (as supplied) |
|---|---|---|
| Part A | Lauryl PEG/PPG-18/18 Methicone | 3.00 |
| | C30-45 Alkyl Methicone (and) C30-45 Olefin | 2.00 |
| | Ethylhexyl Methoxycinnamate | 7.50 |
| | Isoamyl p-Methoxycinnamate | 3.50 |
| Part B | Cyclohexasiloxane (and) Cyclopentasiloxane | 8.50 |
| Part C | Water | Qs to 100 |
| | Glycerin | 4.00 |
| | Sodium Chloride | 1.00 |

| Example B25: | Addition of 10% PMMA polymerisate according to Preparation Example A106 in the water phase of base formation 9 |
|---|---|
| Example B26: | Addition of 2% Bis-Ethylhexyloxyphenol Methoxyphenyl Triazine in the oil phase of the Base formulation 9 as comparative example |

The components of B25, and B26 respectively are incorporated in the base formulation 9 at 50 to 60° C. with stirring.

The samples are applied on sand blasted PMMA plates (delivered by Helioscience, Marseille, France) with a concentration of 1.4 mg/cm$^2$, irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper12.

Results:

|  | Example B25 | Example B26 |
|---|---|---|
| In vitro SPF | 16 | 15 |

Basis Formulation 10: O/W Anionic (10% OCR; 2.6% BMDBM, 0.5% Tinosorb S. 1.6% $TiO_2$)

|  | INCI-Name | % w/w (as supplied) |
|---|---|---|
| Part A | Phenethyl Benzoate | 6.00 |
|  | Cetearyl Ethylhexanoate | 2.00 |
|  | Glyceryl Stearate | 4.00 |
|  | Cetearyl Alcohol (and) PEG-20 Stearate | 3.00 |
|  | Potassium Cetyl Phosphate | 2.00 |
|  | Butyl Methoxydibenzoylmethane | 2.60 |
|  | Octocrylene | 10.00 |
|  | Bis-Ethylhexyloxyphenol Methoxyphenyl Triazine | 0.50 |
|  | Titanium Dioxide (and) Aluminum Hydroxide (and) Stearic Acid | 1.60 |
| Part B | Aqua | Qs to 100 |
|  | Propylene Glycol | 3.50 |
|  | Sodium EDTA | 0.20 |
|  | Xanthan Gum | 0.15 |
| Part C | Propylene Glycol (and) Diazolidinyl Urea (and) Methylparaben (and) Propylparaben | 0.70 |
| Part D | Triethanolamine | qs |

| Example B27: | Addition of 10% PMMA polymerisate according to Preparation Example A106 in the water phase of base formation 10 |
|---|---|
| Example B28: | Addition of 2% Bis-Ethylhexyloxyphenol Methoxyphenyl Triazine in the oil phase of the Base formulation 10 as comparative example |

The components of B27 and B28 respectively are incorporated in the base formulation 10 at 50 to 60° C. with stirring.

The samples are applied on sand blasted PMMA plates (delivered by Helioscience, Marseille, France) with a concentration of 1.4 mg/cm², irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper12.

Results

|  | Example B27 | Example B28 |
|---|---|---|
| In vitro SPF | 25.1 | 18.1 |

Basis Formulation 11: W/O (10% OCR: 2.6% BMDBM, 0.5% Tinosorb S 1.6% $TiO_2$)

|  | INCI-Name | % w/w (as supplied) |
|---|---|---|
| Part A | Phenethyl Benzoate | 5.00 |
|  | Microcrystalline Wax | 1.50 |
|  | Mineral Oil | 3.50 |
|  | Isohexadecane | 3.50 |
|  | Bis-Ethylhexyloxyphenol Methoxyphenyl Triazine | 0.50 |
|  | Octocrylene | 10.00 |
|  | Cetyl Alcohol | 1.50 |
|  | Butyl Methoxydibenzoylmethane | 2.60 |
|  | Titanium Dioxide (and) Stearic Acid (and) Alumina | 1.60 |
|  | Hydrogenated Castor Oil | 1.00 |
|  | PEG-30 Dipolyhydroxystearate | 3.50 |
|  | PEG-22/Dodecyl Glycol Copolymer | 1.80 |
| Part B | Aqua | Qs to 100 |
|  | Propylene Glycol | 4.00 |
|  | Hydrated Magnesium Sulfate | 0.70 |
|  | Sodium EDTA | 0.20 |
|  | Glycerin | 2.00 |
| Part C | Diazolidinyl Urea (and) Methyl paraben (and) Propyl paraben (and) Propylene Glycol | 0.50 |

| Example B29: | Addition of 10% PMMA polymerisate according to Preparation Example A106 in the water phase of base formation 11 |
|---|---|
| Example B30: | Addition of 2% Bis-Ethylhexyloxyphenol Methoxyphenyl Triazine in the oil phase of the Base formulation 11 as comparative example |

The components of B29 and B30 respectively are incorporated in the base formulation 11 at 50 to 60° C. with stirring.

The samples are applied on sand blasted PMMA plates (delivered by Helioscience, Marseille, France) with a concentration of 1.4 mg/cm², irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper12.

Results

|  | Example B29 | Example B30 |
|---|---|---|
| In vitro SPF | 48.3 | 36.0 |

Basis Formulation 12:

|  |  | Examples | | | | | | | |
|---|---|---|---|---|---|---|---|---|---|
|  | INCI-Name | B31 % w/w (as supplied) | B32 % w/w (as supplied) | B33 % w/w (as supplied) | B34 % w/w (as supplied) | B35 % w/w (as supplied) | B36 % w/w (as supplied) | B37 % w/w (as supplied) | B38 % w/w (as supplied) |
| Part A | Phenethyl Benzoate | 5.00 | 5.00 | 5.00 | 5.00 | 5.00 | 5.00 | 5.00 | 5.00 |
|  | Cetearyl Ethylhexanoate | 4.00 | 4.00 | 4.00 | 4.00 | 4.00 | 4.00 | 4.00 | 4.00 |
|  | Glyceryl Stearate | 4.00 | 4.00 | 4.00 | 4.00 | 4.00 | 4.00 | 4.00 | 4.00 |

-continued

|  | INCI-Name | B31 % w/w (as supplied) | B32 % w/w (as supplied) | B33 % w/w (as supplied) | B34 % w/w (as supplied) | B35 % w/w (as supplied) | B36 % w/w (as supplied) | B37 % w/w (as supplied) | B38 % w/w (as supplied) |
|---|---|---|---|---|---|---|---|---|---|
|  | Cetearyl Alcohol (and) PEG-20 Stearate | 2.50 | 2.50 | 2.50 | 2.50 | 2.50 | 2.50 | 2.50 | 2.50 |
|  | Potassium Cetyl Phosphate | 2.00 | 2.00 | 2.00 | 2.00 | 2.00 | 2.00 | 2.00 | 2.00 |
|  | Butyl Methoxydibenzoylmethane | 2.00 | 2.00 | 2.00 | 2.00 | 2.00 | 2.00 | 2.00 | 2.00 |
|  | Octocrylene | 8.00 | 8.00 | 8.00 | 8.00 | 8.00 | 8.00 | 8.00 | 8.00 |
|  | Bis-Ethylhexyloxyphenol Methoxyphenyl Triazine | 2.00 |  | 2.00 |  | 2.00 |  | 2.00 |  |
| Part B | Water | 58.40 | 49.60 | 66.72 | 57.92 | 68.92 | 60.12 | 65.51 | 56.71 |
|  | Propylene Glycol | 3.50 | 3.50 | 3.50 | 3.50 | 3.50 | 3.50 | 3.50 | 3.50 |
|  | Sodium EDTA | 0.20 | 0.20 | 0.20 | 0.20 | 0.20 | 0.20 | 0.20 | 0.20 |
|  | Xanthan Gum | 0.15 | 0.15 | 0.15 | 0.15 | 0.15 | 0.15 | 0.15 | 0.15 |
| Part C | Water | 10.00 | 10.00 |  |  |  |  |  |  |
|  | Phenylbenzimidazole Sulfonic Acid | 2.30 | 2.30 |  |  |  |  |  |  |
|  | Triethanolamine | 1.26 | 1.26 |  |  |  |  |  |  |
|  | Titanium Dioxide (and) Hydrated Silica (and) Aluminum Hydroxide (and) Alginic Acid |  |  |  |  |  |  | 7.10 | 7.10 |
|  | Methylene Bis-Benzotriazolyl Tetramethylbutylphenol (and) Aqua (and) Decyl Glucoside (and) Propylene Glycol (and) Xanthan Gum |  |  | 6.00 | 6.00 |  |  |  |  |
|  | Tris-Biphenyl Triazine |  |  |  |  | 4.00 | 4.00 |  |  |
|  | Preparation Example A106 |  | 10.00 |  | 10.00 |  | 10.00 |  | 10.00 |
| Part C | Propylene Glycol (and) Diazolidinyl Urea (and) Methylparaben (and) Propylparaben | 0.70 | 0.70 | 0.70 | 0.70 | 0.70 | 0.70 | 0.70 | 0.70 |
| Part E | Triethanolamine | qs | qs | qs | qs | qs | qs | qs |  |

Basis Formulation 13:

| INCI | Example B39 | B40 |
|---|---|---|
| Lauryl PEG-9 Polydimethylsiloxyethyl Dimethicone | 3.00 | 3.00 |
| Ethylhexyl Benzoate | 13.00 | 8.00 |
| Dimethicone (and) Trimethylsiloxysilicate | 1.00 | 1.00 |
| Cyclopentasiloxane | 11.00 | 11.00 |
| Caprylyl Methicone | 11.00 | 11.00 |
| Ethylhexyl Methoxycinnamate | 7.00 | 7.00 |
| Zinc Oxide (and) Dimethicone/Methicone Copolymer | 8.30 | 8.30 |
| Cyclomethicone (and) Titanium Dioxide (and) Bis-PEG/PPG-14/14 Dimethicone | 5.00 | 5.00 |
| Bis-Ethylhexyloxyphenol Methoxyphenyl Triazine | 3.00 | 0.00 |
| Water | 16.10 | 13.10 |
| Tocopheryl Acetate | 3.00 | 3.00 |
| Butylene Glycol | 3.00 | 3.00 |
| Sodium Chloride | 1.00 | 1.00 |
| Disodium EDTA | 0.20 | 0.20 |
| Alcohol | 7.00 | 7.00 |
| Preparation Example A106 | 0.00 | 10.00 |
| Polymethylsilsesquioxane | 4.00 | 4.00 |
| Silica | 3.00 | 3.00 |
| Phenonip | 0.40 | 0.40 |

The invention claimed is:

1. A cosmetic composition comprising
a concentrated aqueous polymer dispersion for the protection of human or animal hair or skin against the damaging effects of UV radiation comprising particles with an average particle size of less than 1000 nm; and a cosmetically acceptable carrier, wherein the particles of the concentrated aqueous polymer dispersion comprise:

(a) a polymer carrier prepared by heterophase radical polymerization of at least one ethylenically unsaturated monomer in the presence of (b) at least one oil-soluble organic UV absorber of ($b_2$);

wherein ($b_2$) is Bis-Ethylhexyloxyphenol Methoxyphenyl Triazine of formula (2);

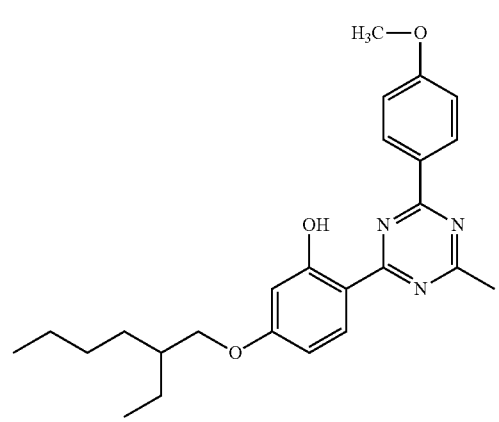

-continued

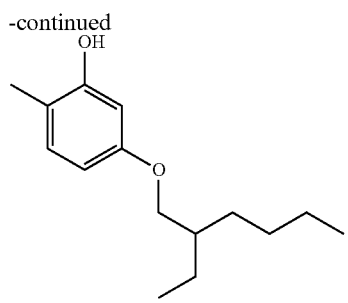

wherein the at least one ethylenically unsaturated monomer is selected from the group consisting of $C_1$-$C_{18}$ acrylates, $C_1$-$C_{18}$ methacrylates, acrylic acid, (meth)acrylic acid, styrene, vinyltoluene, hydroxy-functional acrylates or (meth)acrylates, acrylates or (meth)acrylates derived from alkoxylated alcohols, multifunctional acrylates or (meth)acrylates, and mixtures thereof;

wherein the weight ratio of the oil-soluble organic UV absorber (b) to polymer carrier (a) in the particles is equal to or greater than 80 parts UV absorber per 100 parts of polymer carrier;

wherein the concentration of the particles of the polymer carrier with the oil-soluble organic UV absorber in the dispersion is more than 50% and up to 60% b.w.; and wherein the at least one oil-soluble organic UV absorber (b) is dissolved in the at least one ethylenically unsaturated monomer before the heterophase radical polymerization.

2. The composition according to claim 1 wherein the average particle size is less than 500 nm.

3. The composition according to claim 1 comprising additionally a non-ionic, cationic or anionic surfactant.

4. The composition according to claim 1 wherein the oil-soluble organic UV absorber (b) has a water solubility of less than 1% by weight at room temperature and atmospheric pressure.

5. The cosmetic composition according to claim 1 in which is an aqueous environment/media/formulation.

6. The cosmetic composition according to claim 1, further comprising
    from 1 to 60% by weight, based on the total weight of the composition, of at least one oil component,
    from 0 to 30% by weight, based on the total weight of the composition, of at least one emulsifier,
    from 10 to 90% by weight, based on the total weight of the composition, of water, and
    from 0 to 88.9% by weight of further cosmetically acceptable adjuvants.

7. The cosmetic composition according to claim 1, wherein the heterophase radical polymerization for preparation of the polymer carrier comprises:
    (i) dissolving the oil-soluble organic UV absorber (b) in at least one ethylenically unsaturated monomer (a);
    (ii) preparing a conventional o/w emulsion of said UV absorber (b) dissolved in at least one ethylenically unsaturated monomer (a);
    (iii) homogenizing the conventional emulsion to a miniemulsion wherein the droplets of the organic phase have an average diameter below 1000 nm; and
    (iv) polymerizing the miniemulsion by adding a polymerization initiator.

8. The composition according to claim 1 wherein the polymer carrier consists of a polymerization reaction product of (i) the at least one ethylenically unsaturated monomer and (ii) optionally 0.5 to 20 wt. % ethylenically unsaturated multifunctional crosslinking monomers based on the total weight of monomers forming the polymerization reaction product.

* * * * *